(12) United States Patent
Groenhuis et al.

(10) Patent No.: US 11,898,581 B2
(45) Date of Patent: Feb. 13, 2024

(54) PNEUMATIC STEPPER MOTOR AND DEVICE COMPRISING AT LEAST ONE SUCH PNEUMATIC STEPPER MOTOR

(71) Applicant: Machnet SG PTE. LTD., Singapore (SG)

(72) Inventors: Vincent Groenhuis, Enschede (NL); Francoise Jeanette Siepel, Tubbergen (NL); Stefano Stramigioli, Borne (NL)

(73) Assignee: Machnet Medical Robotics B.V., Heerenveen (NL)

( * ) Notice: Subject to any disclaimer, the term of this patent is extended or adjusted under 35 U.S.C. 154(b) by 826 days.

(21) Appl. No.: 16/326,442

(22) PCT Filed: Aug. 23, 2017

(86) PCT No.: PCT/NL2017/050552
§ 371 (c)(1),
(2) Date: Feb. 19, 2019

(87) PCT Pub. No.: WO2018/038608
PCT Pub. Date: Mar. 1, 2018

(65) Prior Publication Data
US 2020/0182267 A1 Jun. 11, 2020

Related U.S. Application Data

(60) Provisional application No. 62/522,734, filed on Jun. 21, 2017, provisional application No. 62/378,261, filed on Aug. 23, 2016.

(51) Int. Cl.
*F15B 15/06* (2006.01)
*F15B 11/12* (2006.01)
(Continued)

(52) U.S. Cl.
CPC ........ *F15B 15/065* (2013.01); *A61B 10/0041* (2013.01); *F15B 11/12* (2013.01); *F15B 11/127* (2013.01); *A61B 2010/0208* (2013.01)

(58) Field of Classification Search
CPC ..... F15B 15/065; F15B 11/127; B23Q 16/023
See application file for complete search history.

(56) References Cited

U.S. PATENT DOCUMENTS 3,596,526 A * 8/1971 Gribble ............... B23Q 16/023
74/110
4,545,288 A * 10/1985 Burke .................... F01B 9/047
92/136

(Continued)

FOREIGN PATENT DOCUMENTS

DE 19808211 A1 11/1999
DE 102004019766 A1 11/2005
(Continued)

OTHER PUBLICATIONS

Improving Accuracy and Efficiency in MRI-navigated Breast Biopsy by Vincent Groenhuis (Year: 2014).*
(Continued)

*Primary Examiner* — Kenneth Bomberg
*Assistant Examiner* — Michael Quandt
(74) *Attorney, Agent, or Firm* — KDW Firm PLLC

(57) ABSTRACT

A pneumatic stepper motor includes a housing, said housing accommodating at least part of: a rack or geared axle comprising a plurality of gear elements; and two pistons, each comprising at least two teeth, said pistons being arranged to cooperate with said rack or geared axle. The racks may either be straight or curved. The pistons are preferably double-acting pistons. A device includes at least one, and preferably a plurality of, such pneumatic stepper motor(s). The device may in particular be an MRI-compat-
(Continued)

Figure 1A:
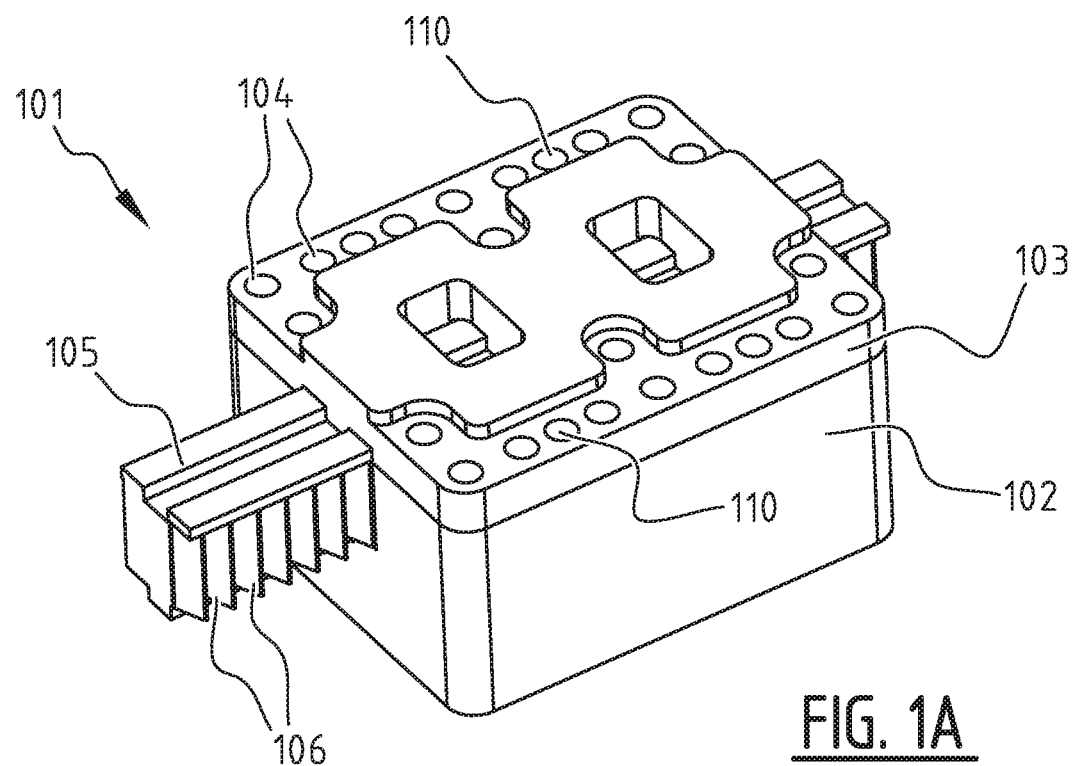

ible robotic system, more in particular for example an MRI-guided breast biopsy device.

13 Claims, 26 Drawing Sheets

(51) Int. Cl.
*A61B 10/00* (2006.01)
*A61B 10/02* (2006.01)

(56) References Cited

U.S. PATENT DOCUMENTS

| | | | | |
|---|---|---|---|---|
| 7,530,189 | B2* | 5/2009 | Kim | F24F 1/0057 40/725 |
| 8,984,871 | B1* | 3/2015 | Probst | F15B 11/08 92/13 |

FOREIGN PATENT DOCUMENTS

| | | | |
|---|---|---|---|
| GB | 910203 A | * | 11/1962 |
| JP | 2011241970 A | | 12/2011 |
| NL | 250969 A | | 2/1964 |
| WO | 9005617 A1 | | 5/1990 |

OTHER PUBLICATIONS

Groenhuis Vincent et al: "Laser-Cutting Pneumatics", IEEE/ASME Transactions on Mechatronics, IEEE Service Center, Piscataway, NJ, US, vol. 21, No. 3, Jun. 3, 2016 (Jun. 3, 2016), pp. 1604-1611, XP011611210, ISSN: 1083-4435, DOI: 10.1109/TMECH.2015. 2508100 [retrieved on May 2, 2016].

International Search Report and Written Opinion for the International Patent Application No. PCT/NL2017/050552, dated Aug. 12, 2017.

\* cited by examiner

Figure 23

| Motor | Max. force/torque | Efficiency |
|---|---|---|
| T-63 | 330 N | 76% |
| T-49 | 100 N | 65% |
| R-80 | 3.7 N m | 50% |
| R-44 | 0.48 N m | 63% |
| R-25 | 0.10 N m | 66% |

Figure 24

| Motor | Max. unloaded speed |
|---|---|
| T-63 | 200 steps/s = 200 mm/s |
| T-49 | 320 steps/s = 320 mm/s |
| R-80 | 80 steps/s = 133 rpm |
| R-44 | 200 steps/s = 333 rpm |
| R-25 | 200 steps/s = 231 rpm |

Figure 25

| Motor | Max. power | Force/torque and frequency |
|---|---|---|
| T-63 | 26 W | 250 N, 105 Hz |
| T-49 | 15 W | 100 N, 150 Hz |
| R-80 | 25 W | 2.6 N m, 55 Hz |
| R-44 | 3.7 W | 0.28 N m, 75 Hz |
| R-25 | 1.1 W | 0.059 N m, 160 Hz |

Figure 26

| coordinate | $\mu$ | $\sigma$ |
|---|---|---|
| X | 0.46 mm | 0.71 mm |
| Z | 0.10 mm | 0.21 mm |

Figure 27

| Property | T-26 (Stormram 4) | T-49 (Stormram 3) |
|---|---|---|
| Dimensions | 26x21x16 mm | ⌀56x40 mm / 49x40x31 mm |
| Volume | 8.7 cm³ | 99 cm³ / 61 cm³ |
| Force at 0.4 MPa | 38 N | 96 N |
| Step size | 0.25 mm | 1.0 mm |

Figure 28

PNEUMATIC STEPPER MOTOR AND DEVICE COMPRISING AT LEAST ONE SUCH PNEUMATIC STEPPER MOTOR

This is a national stage application filed under 35 U.S.C. § 371 of pending international application PCT/NL2017/050552 filed Aug. 23, 2017, which claims priority to U.S. provisional patent application No. 62/378,261, filed Aug. 23, 2016, and which also claims priority to U.S. provisional patent application No. 62/522,734, filed Jun. 21, 2017, the entirety of which applications are hereby incorporated by reference herein.

The invention relates to a pneumatic stepper motor. The pneumatic stepper motor according to the invention is preferably lightweight and/or completely metal-free and/or fully customizable. Applications of the pneumatic stepper motor might include MRI-compatible robotic systems, high-voltage switchgear or nuclear power plant systems which restrict electric actuation, and/or other actuation systems where pressurized air is available and/or lightweight actuators are preferred.

Rotational stepper motors are widely used in actuation of mechanical devices. Off-the-shelf stepper motors are generally driven by electromagnetic forces, constructed from an electromagnetic stator and a permanent magnet rotor. The stator has two or more phases, each consisting of an electromagnetic coil which can generate a magnetic field to apply a torque on the rotor. By driving the coils with appropriate waveforms, step-wise rotational motion is achieved. A rack-and-pinion or leadscrew mechanism can convert rotational to translational movements, but pure electromagnetic linear stepper motors also exist in which the stator is a track of magnets on which a moving platform with electromagnetic coils can slide back and forth.

In certain applications, a metal-free stepper motor is required. MRI-compatible robotic systems need to be driven by motors that do not affect the magnetic field of the MRI scanner, requiring them to be metal-free when placed inside the MRI bore near the scanning volume. Other possible applications are in the field of high-voltage switchgear such as circuit breakers or in the field of nuclear power plant systems, where electric actuation of mechanical switches is complicated due to the high voltages or radiation involved.

The invention may in particular relate to a pneumatic stepper motor that can be constructed using rapid prototyping techniques such as 3D printing and laser-cutting. Rapid prototyping functional mechanisms by additive manufacturing is booming. Fused filament fabrication (FFF) printers extrude plastic materials such as acrylonitrile butadiene styrene (ABS) or polyactic acid (PLA) on a layer-by-layer basis, creating rigid structures. Several parts can then be assembled together to create passive, complex mechanical devices. For actuation of such devices, there is a strong request for designs of actuators that can be rapid prototyped as well.

One goal of the motors presented by way of example in this application is actuation of MRI-compatible robotics. As an example, the current manual MRI-guided breast biopsy procedure is inaccurate and would benefit from a robotically-driven needle positioning and insertion system that can operate inside the bore.

Electromagnetic stepper motors and DC motors distort the magnetic field and are not MRI-compatible. Various alternative actuation methods have been investigated; while hydraulic, piezo, cable transmission, MRI-driven, air turbine, flexible fluidic actuators, direct-acting pneumatic actuators and unidirectional pneumatic stepper motors have been demonstrated, actuation by metal-free bidirectional pneumatic stepper motors is the most popular approach because this is inherently MRI-compatible and can be easily controlled with a standard pneumatic valve manifold.

Figure 23:
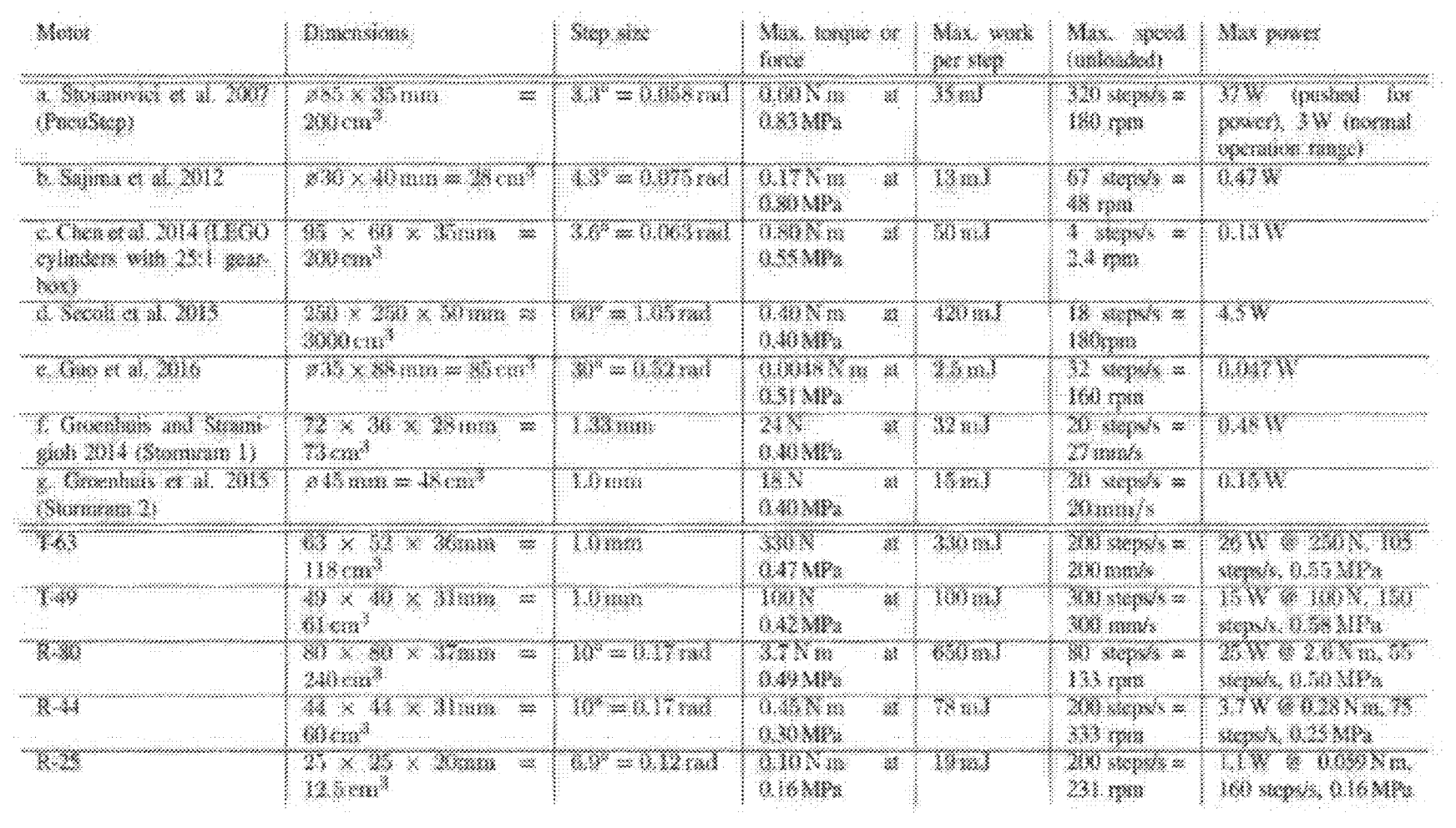

FIG. 23 lists a number of MRI-compatible pneumatic stepper motors found in literature. These can be compared by specifications such as motor dimensions, step size, force, stepping frequency and power. Because there is no uniform test protocol, not all figures are directly comparable. This especially applies to the maximum power, for which certain authors push the motor outside the normal operation range using short tubes, high pressure and fast valves, while other authors only perform measurements using a practical setup with longer tubes and/or slower valves. It might therefore also be useful to compare the maximum work (force times displacement) performed in one single step, hereby ignoring the stepping frequency.

Stoianovici et al. developed the PneuStep. This design avoids sliding parts as much as possible by using diaphragm sealing and ball bearings. It provides 3 W output power in normal operation range, and up to 37 W when pushed for power. However, the PneuStep design is relatively large and also very complex to manufacture due to the 26 different components made out of 11 materials. The design of Sajima et al. is much compacter and easy to manufacture, and still offers good properties considering its size. The Lego-powered motor by Chen et al. performs much work per step and uses a gearbox to obtain high output torque, but it was only tested at low speeds (4 steps/sec) resulting in a rated power of 0.13 W which is rather weak for its size. Also, it makes use of commercial Lego cylinders, limiting the rapid prototypeability. Secoli et al. developed a powerful three-piston motor, but it is huge in size and has many components. The design of Guo et al. is innovative and easy to manufacture, but the current prototype is not yet powerful enough to perform effective work.

US2014/0076087 discloses a motor system comprising a motor comprising a rack having a periodic surface thereon which is engaged by a plurality of engaging elements. By driving the engaging elements back and forth towards the surface structure in a periodic and time shifted manner, a linear motion can be brought about.

Besides rotational stepper motors which could drive a spindle or rack-and-pinion mechanism to actuate linear motion, true linear stepper motors also have been developed. The authors of this paper, Groenhuis et al. developed two designs of different sizes produced by laser-cutting (and 3d printing), delivering up to 24 N of force. Due to the choice of valves, it has only been tested at speeds up to 20 steps/s, delivering 0.48 W for the 2014 design as used in the Stormram 1 robot, and 0.15 W for the more compact 2015 design in the Stormram 2 robot.

It is an aim of the invention to overcome any of the above described drawbacks. In particular, it may be an aim of the invention to provide a pneumatic stepper motor that is lightweight and/or completely metal-free and/or fully customizable.

In order to achieve this objective the pneumatic stepper motor in accordance with the invention comprises:
- a housing, said housing accommodating at least part of:
  - a rack or geared axle comprising a plurality of gear elements, and
  - two pistons, each comprising at least two teeth, said pistons being arranged to cooperate with said rack or geared axle.

The housing, rack or geared axle, and the two pistons may each be separately made, and may then be assembled to form said pneumatic stepper motor. The two pistons are preferably identical to each other. Because the pneumatic stepper motor according to the invention comprises only a few different components, it is easy to manufacture.

It is further noted, that said pneumatic stepper motor may comprise more elements, such as for example a third or even higher number of pistons.

In an embodiment of the pneumatic stepper motor according to the invention, said pneumatic stepper motor further comprises at least one pneumatic tube connected to said housing that is arranged to supply air to the housing in order to drive said pistons in a reciprocating movement.

The at least one pneumatic tube may be any suitable pneumatic tube that is generally available for sale.

The housing may comprise at least one connector for connecting the pneumatic tube thereto. For example said connector may comprise a socket arranged in said housing for accommodating an end part of the pneumatic tube.

The pneumatic tube may connect to a chamber or bore of the housing in which the piston is arranged.

In another embodiment of the pneumatic stepper motor according to the invention the housing comprises two chambers or bores, each accommodating one of the two pistons, wherein four pneumatic tubes are provided, each pneumatic tube being connected to a different longitudinal end of the two chambers or bores, for example via a said connector, for supplying air to one longitudinal end at a time in order to drive a respective piston in the direction of the other longitudinal end of that bore or chamber. In such an embodiment air may be selectively supplied to one longitudinal end at a time via a respective pneumatic tube connected to that longitudinal end. In particular air may be selectively supplied to the different ends in a chosen sequence, in order to drive the pistons in accordance with said chosen sequence in a reciprocating movement.

Because the pistons are accommodated in the chambers or bores of the housing, the housing and rack or geared axle may be moved with respect to each other.

In another embodiment of the pneumatic stepper motor according to the invention said rack is a substantially straight or curved elongated rack, thereby forming a linear or curved pneumatic stepper motor, respectively.

The curvature and in particular the radius thereof may be chosen as desired.

In yet another embodiment of the pneumatic stepper motor according to the invention said rack comprises said gear elements at at least two longitudinal sides thereof.

An advantage thereof is that pistons may engage with said gear elements at two longitudinal sides of the rack. This may provide a relatively compact pneumatic stepper motor, because is it not required that all pistons need to be provided next to each other at one longitudinal side of the rack, but may be provided at substantially the same longitudinal positon along the length of the rack at said two longitudinal sides.

The longitudinal sides may in particular be two opposing longitudinal sides.

The gear elements at the two longitudinal sides are preferably offset with respect to each other. For example, if said gear elements are formed by second teeth, the second teeth at the two longitudinal sides may be offset with respect to each other, such that the top or valley of a second teeth at one longitudinal side is offset with respect to, or not in line with, the top or valley, respectively, of a second teeth at the other longitudinal side.

In yet another embodiment of the pneumatic stepper motor according to the invention said geared axle comprises said gear elements evenly distributed over the circumference thereof.

In this embodiment the gear elements may thus have a constant angular pitch distance therebetween. The pitch distance may be chosen as desired.

In particular, said gear elements may be evenly distributed over the circumference of the geared axle at one longitudinal position thereof, i.e. the gear elements are provided in one, substantially circular line.

In yet another embodiment of the pneumatic stepper motor according to the invention said gear elements comprise second teeth, said second teeth extending substantially orthogonal to a longitudinal direction of the rack or substantially radial with respect to a longitudinal axis of the geared axle.

In yet another embodiment of the pneumatic stepper motor according to the invention each piston comprises two engagement surfaces for engagement with the rack or geared axle, said two engagement surfaces being substantially opposite to each other, wherein each engagement surface comprises said at least two teeth.

An advantage of such pistons is that each piston may engage with the gear elements of the rack or geared axle in both reciprocating movement directions thereof. In the first reciprocating movement direction one engagement surface may engage with the rack or geared axle, and in the second, opposite reciprocating movement direction the other engagement surface may engage with the rack or axle. One such "double acting" piston may thus function as two pistons having only one engagement surface. This may thus provide a relative compact pneumatic stepper motor with relative few components.

The four engagement surfaces of the two pistons are preferably driven in an off phase manner with respect to each other and the rack or geared axle, such that at a certain time only one engagement surface engages with the rack or geared axle in such a manner that the piston moves with respect to the rack or geared axle. The phase shift between the engagement surfaces may in particular be chosen to be 90°. Because each piston comprises two opposing engagement surfaces, the phase shift between the opposing engagement surfaces of one piston is 180°. The phase shift between the two pistons may be chosen as desired, preferably 90° as described earlier.

In such an embodiment, if said pneumatic stepper motor comprises a rack, said rack may comprise said gear elements at two opposing longitudinal sides thereof. The two pistons are preferably arranged next to each other along the length of the rack.

In such an embodiment, if said pneumatic stepper motor comprises a geared axle, said geared axle may comprise said gear elements evenly distributed over the circumference thereof, such that, at a certain time, said one engagement surface may engage with the gear elements on one side or part of the geared axle and the other engagement surface may engage with the gear elements on the other, opposing or diametrical side or part of the geared axle. As a result of the reciprocating movement of the piston and the engagement with the gear elements, the piston may rotate with respect to the geared axle. In particular, the geared axle may be rotatably driven as a result of the reciprocating movement of the pistons. The two pistons are preferably directed to a central line of the geared axle under an angle of 90° with respect to each other, such that the engagement surfaces have an angular pitch distance of 90°, wherein an engagement surface of the one piston is distanced with an angular pitch distance of 90° from the neighbouring engagement surface of the other piston.

In yet another embodiment of the pneumatic stepper motor according to the invention said pistons are provided with at least one silicone rubber seal, said seal being arranged on a side of the piston that is opposite to a side from which the teeth extend, wherein said seal is preferably laser-cut from a silicone rubber starting material.

Said seal may provide a seal between the piston and the rack or geared axle, such that air may be prevented from leaking towards said rack or geared axle.

In yet another embodiment of the pneumatic stepper motor according to the invention said pistons each comprise a cavity, wherein the teeth extend in this cavity, and wherein the rack or geared axle is arranged in this cavity, such that the teeth face the gear elements of said rack or geared axle.

The teeth extend into and thereby fill up part of the cavity. In other words, the teeth define an outer circumferential surface of the cavity.

If said piston comprises said two engagement surfaces, a plate like element may extend between the two engagement surfaces and thus between the at least two teeth of each engagement surface. Such a plate like element may thus connect the two engagement surfaces. Said plate like element may define a bottom surface of the cavity.

Said plate like element may comprise an opening for allowing a part of the geared axle to extend thereto.

In yet another embodiment of the pneumatic stepper motor according to the invention said housing comprises a first part and second part, which first and second part are connected to each other using at least one connector, for example screws or glue, and are preferably sealed by a sealant.

In such a manner an airtight housing may be provided. Said sealant may be any suitable type of sealant, for example glue or silicone. Said sealant or glue may perform a double function of both connecting and sealing the two housing parts to each other.

Said first and second part may in particular be a bottom and top part, respectively.

In yet another embodiment of the pneumatic stepper motor according to the invention said housing and/or said rack or geared axle and/or said pistons are manufactured from a suitable material.

Said material may be any suitable material, that is preferably rigid, i.e. has high tensile strength, and/or has low friction and/or low wear, and/or is magnetic radiation safe and/or is 3D printable.

Said material may in particular be chosen from the group comprising: ABS (Acrylonitrile butadiene styrene), PLA (polylactic acid), PETG (Polyethylene terephthalate), Ceramics, PEEK (Polyether ether ketone).

In particular said housing and/or said rack or geared axle and/or said pistons may be manufactured from any such material by 3D printing.

If MRI safety and/or 3D printability is not desired for a particular application, then conventional metals like aluminum, brass, steel etc. are good options.

Instead of 3D printing any other suitable manufacturing method may be used. For example, but not limited thereto, injection molding, milling, cutting, sawing, drilling, or any other technique.

The invention also relates to a device, comprising at least one pneumatic stepper motor as described above or below in any one or more of the embodiments or comprising any one or more feature as described above or below.

In an embodiment of the device according to the invention said device comprises at least one linear pneumatic stepper motor and at least one curved pneumatic stepper motor, in order to be able to move a predetermined part of said device in at least one linear direction along said rack of said linear pneumatic stepper motor and at least part of said predetermined part in at least one curved direction along said rack of said curved pneumatic stepper motor.

Said predetermined part may be moved in two opposing directions along said linear direction.

Said at least part of the predetermined part may be moved in two opposing directions along said curved direction.

In an embodiment said device is an MRI-compatible robotic system.

An advantage of the device according to the invention is that it may be completely made of a plastics material and/or that it at least may not comprise any metal part and/or no electronics, such that the device is MRI-compatible.

The electronics for controlling the air supply may be arranged at a desired distance from the device and in particular in another room. This may require quite long pneumatic tubes, however, apart from some slight delay, this has proven to may be problemless.

More particularly, said device may be an MRI-guided breast biopsy device, wherein said at least part of the predetermined part is a needle holder that is arranged to hold a needle.

In such an embodiment said device preferably comprises two curved pneumatic stepper motors, which two curved racks thereof are preferably arranged substantially vertical, i.e. the longitudinal directions thereof are substantial vertical in use of the device, and with the concave parts thereof directed towards each other, and wherein the needle holder is connected to and able to move along the two curved racks independently, such that said needle holder is able to be moved substantially upwards and downwards and such that an angle between the needle held by said needle holder at least in use of the device and a horizontal plane is adjustable.

In such an embodiment said device preferably comprises a linear stepper motor, which linear rack thereof is arranged substantially parallel to the needle held by said needle holder at least in use of the device, i.e. the longitudinal directions thereof are substantial parallel to each other, wherein the needle holder is connected to and able to move along said linear rack such that said needle holder and thereby the needle held by the needle holder at least in use of the device is able to be moved substantially forwards and backwards in order to be able to puncture and retract from a breast during use of the device.

In such an embodiment said device preferably comprises a further linear or curved stepper motor, which further linear or curved rack thereof is arranged substantially orthogonal to the needle held by said needle holder at least in use of the device, i.e. the longitudinal direction of the rack is substantially orthogonal to the longitudinal direction of the needle held by said needle holder at least in use of the device, and is arranged substantially horizontal, wherein the predetermined part is connected to and able to move along said further linear or curved rack such that said predetermined part is able to be moved substantially sideward with respect to a longitudinal direction of said needle held said needle holder at least in use of the device. If said further stepper motor is a curved stepper motor, the concave side of the further curved rack is preferably directed towards the breast, i.e. towards the needle holder, such that the predetermined part is able to be moved around said breast in a substantially horizontal direction.

Said needle holder may thus preferable be moveable in four directions of freedom using said four pneumatic stepper motors according to the invention.

Said curved and linear stepper motors may be arranged in a serial sequence in order to drive said predetermined part and/or said needle holder in a serial sequence along any of the curved and linear racks.

It is noted that although the MRI-compatible device is a very suitable use of the device, the invention is not limited thereto. The device may be used in any desired and/or suitable way.

For example, the device may be a device for a high-voltage switchgear or nuclear power plant systems which restrict electric actuation, and/or a device for other actuation systems where pressurized air is available and/or lightweight and/or rapid prototypeable actuators are preferred.

Figure 1B:
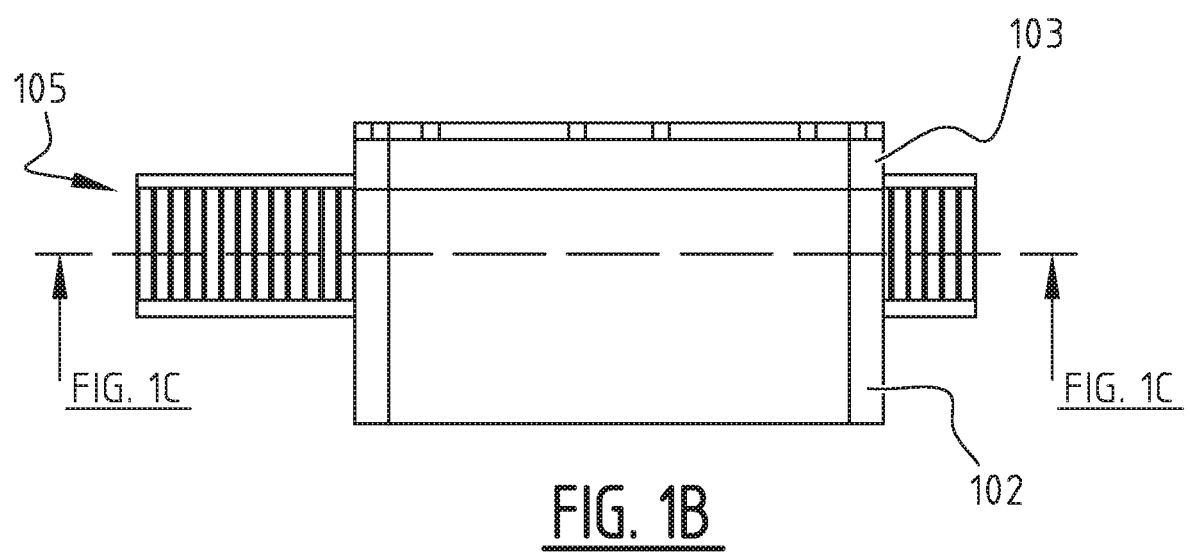
Figure 1C:
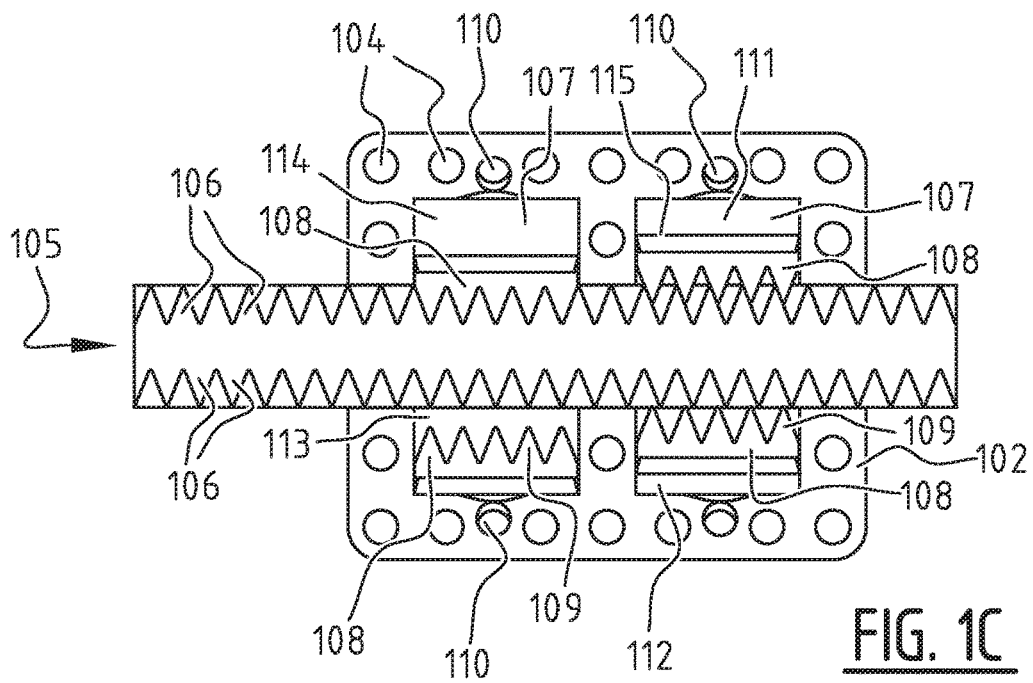
Figure 1D:
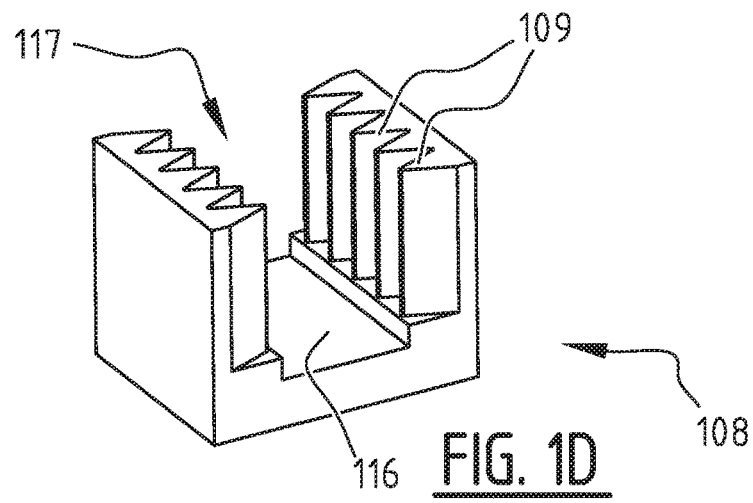
Figure 2:
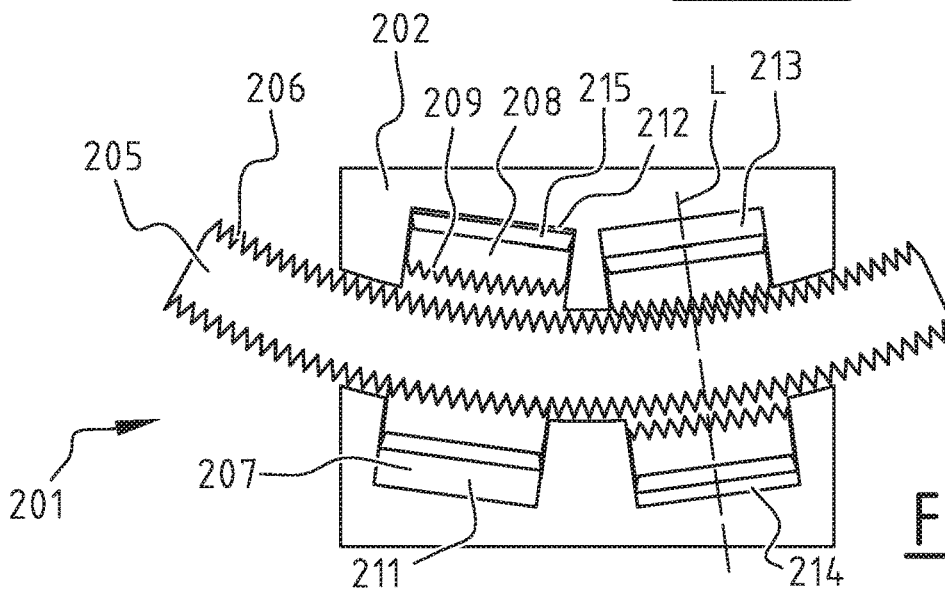
Figure 3A:
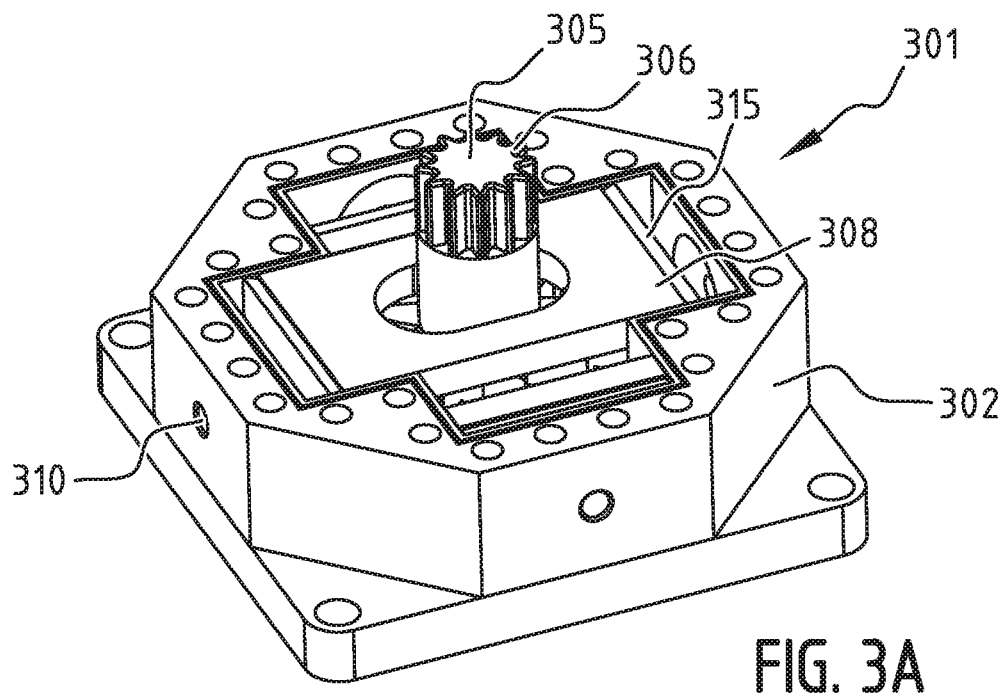
Figure 3B:
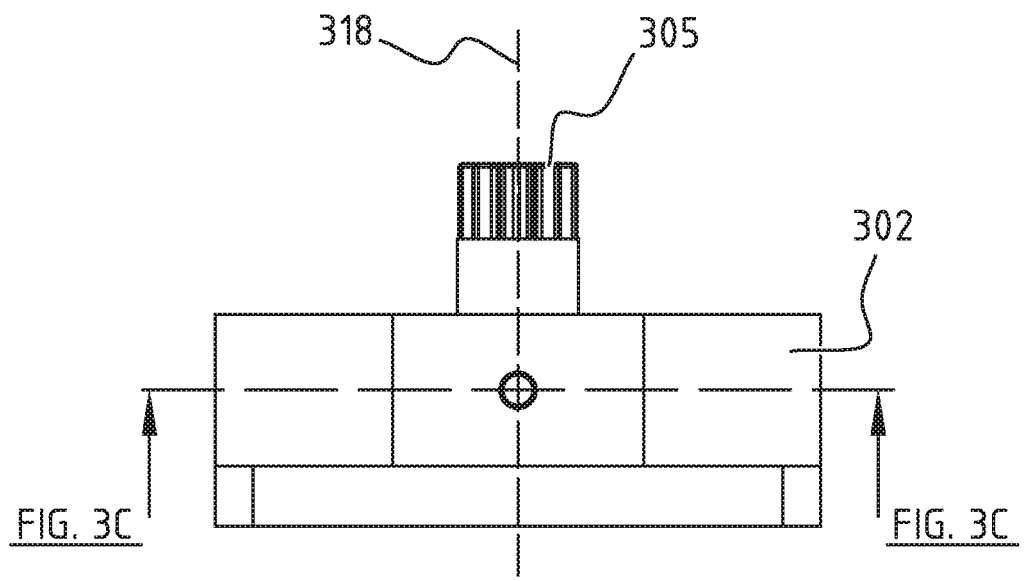
Figure 3C:
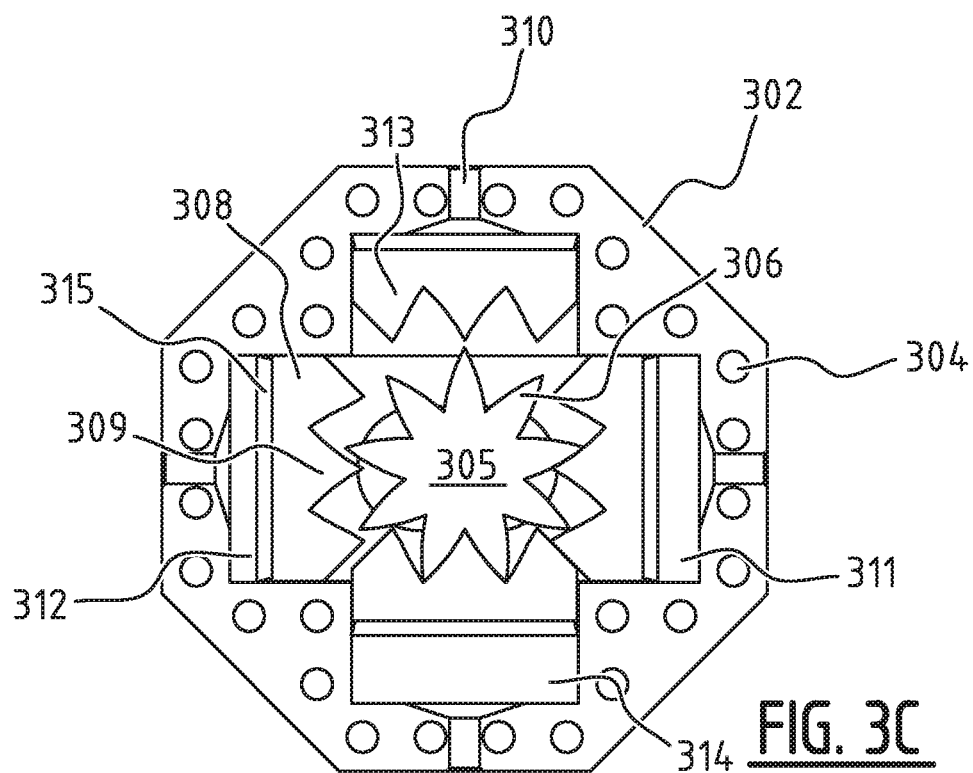
Figure 3D:
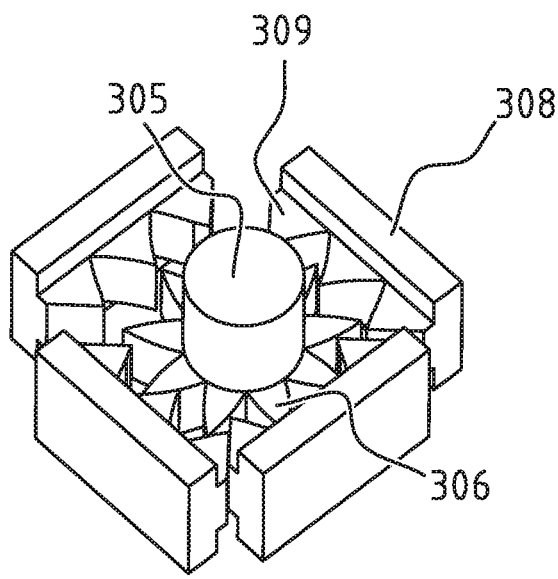
Figure 4A:
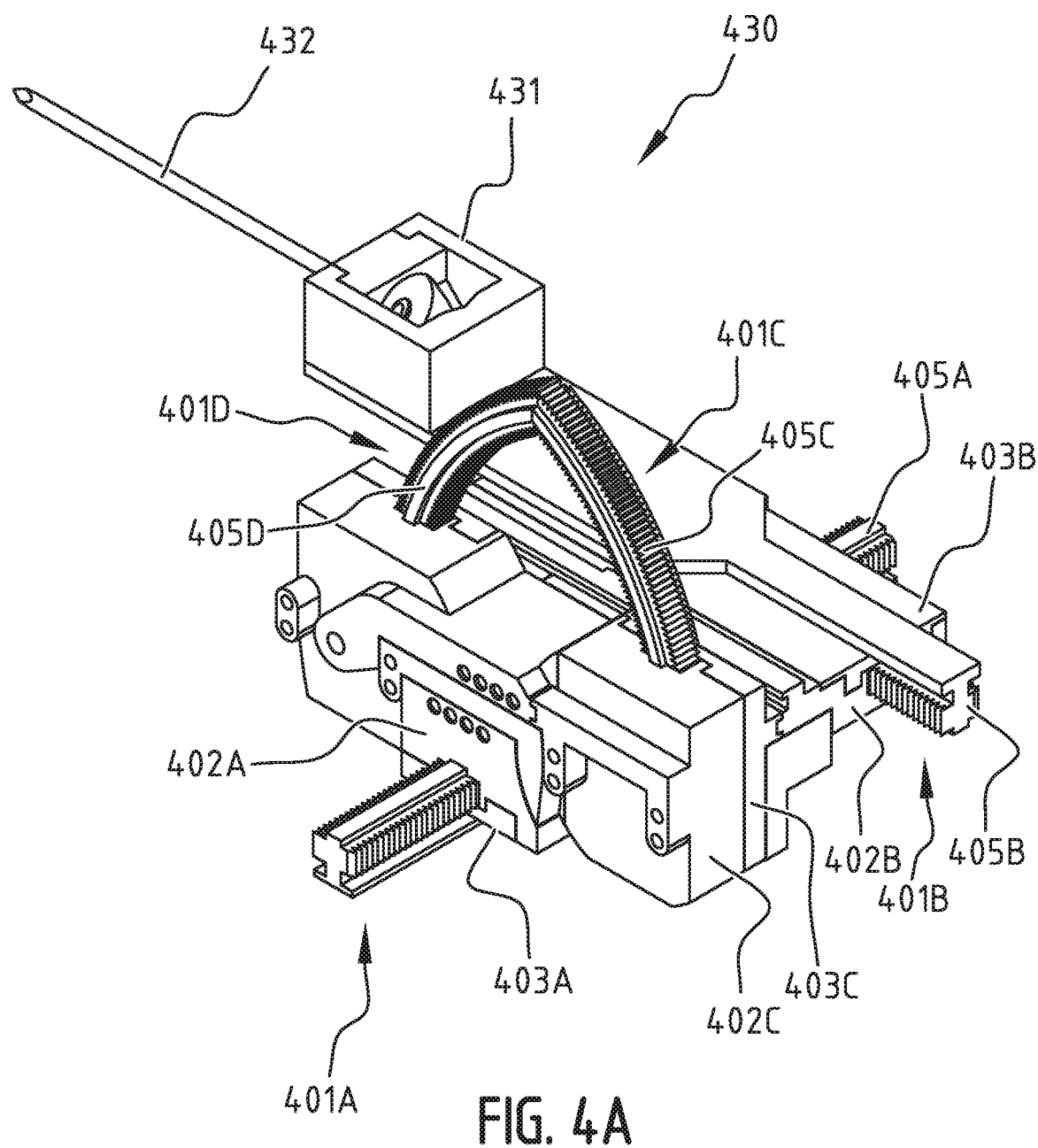
Figure 4B:
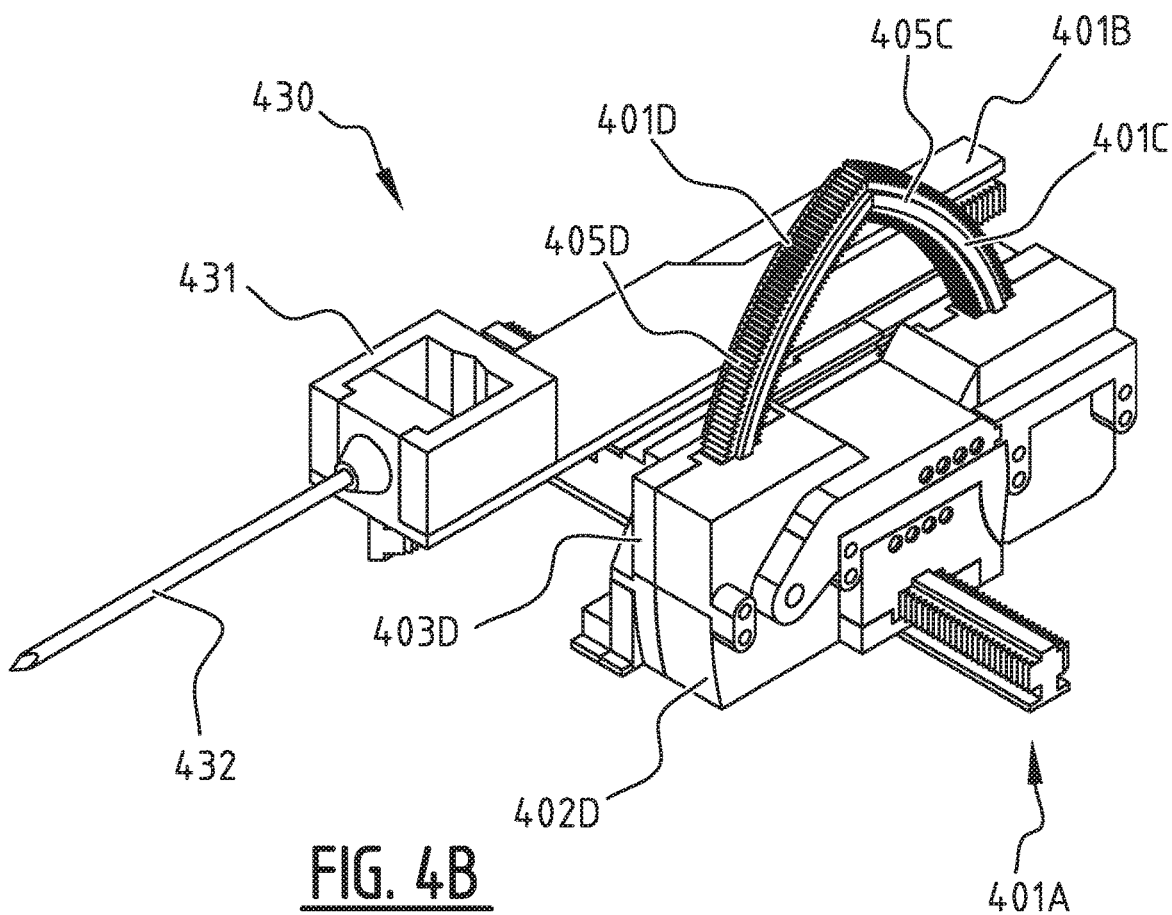
Figure 4C:
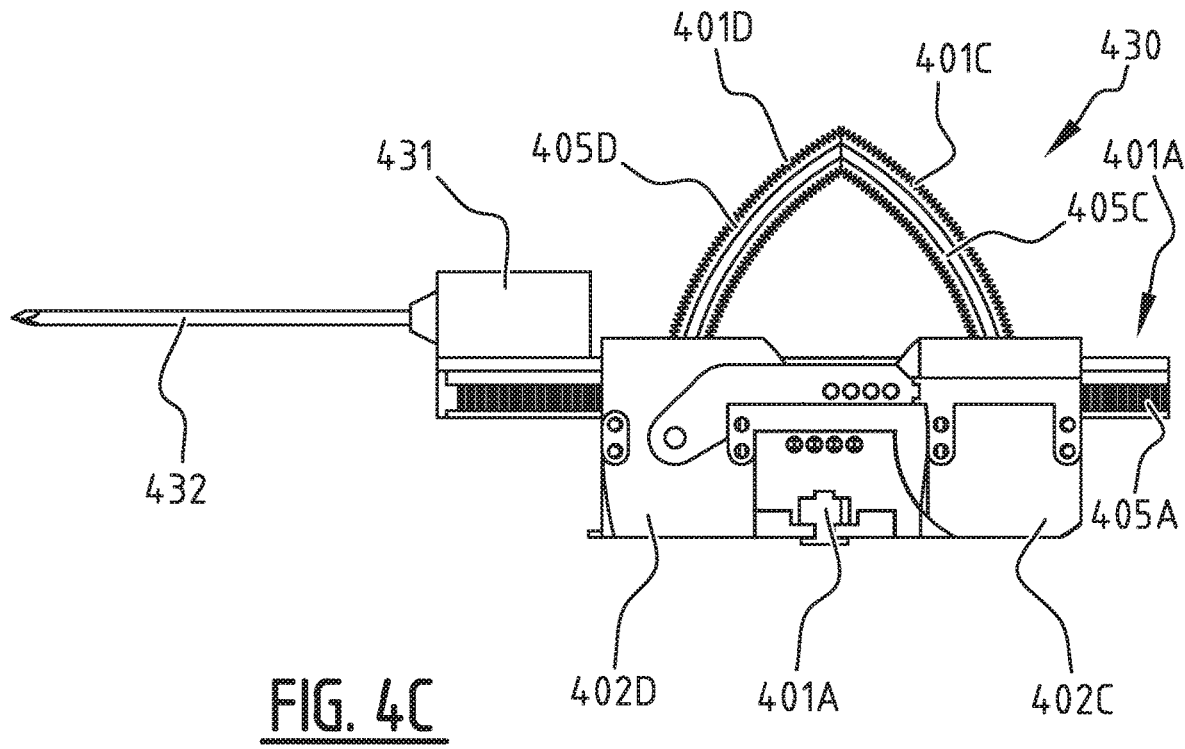
Figure 4D:
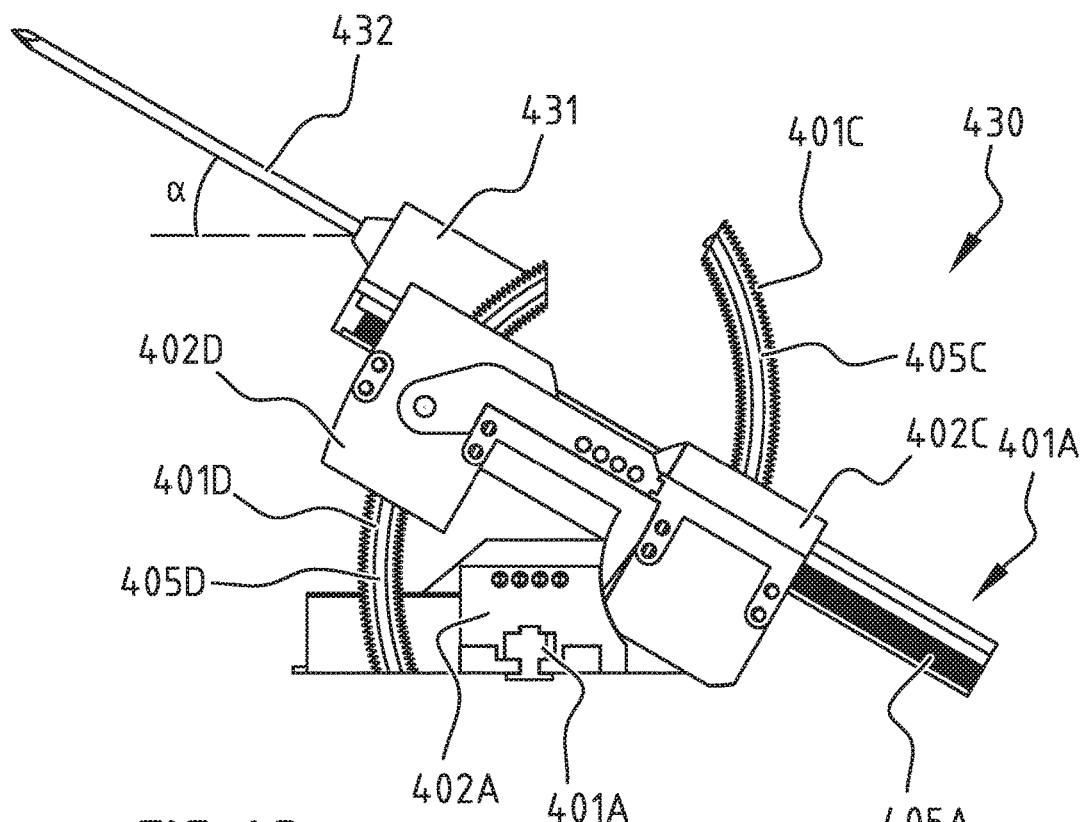
Figure 4E:
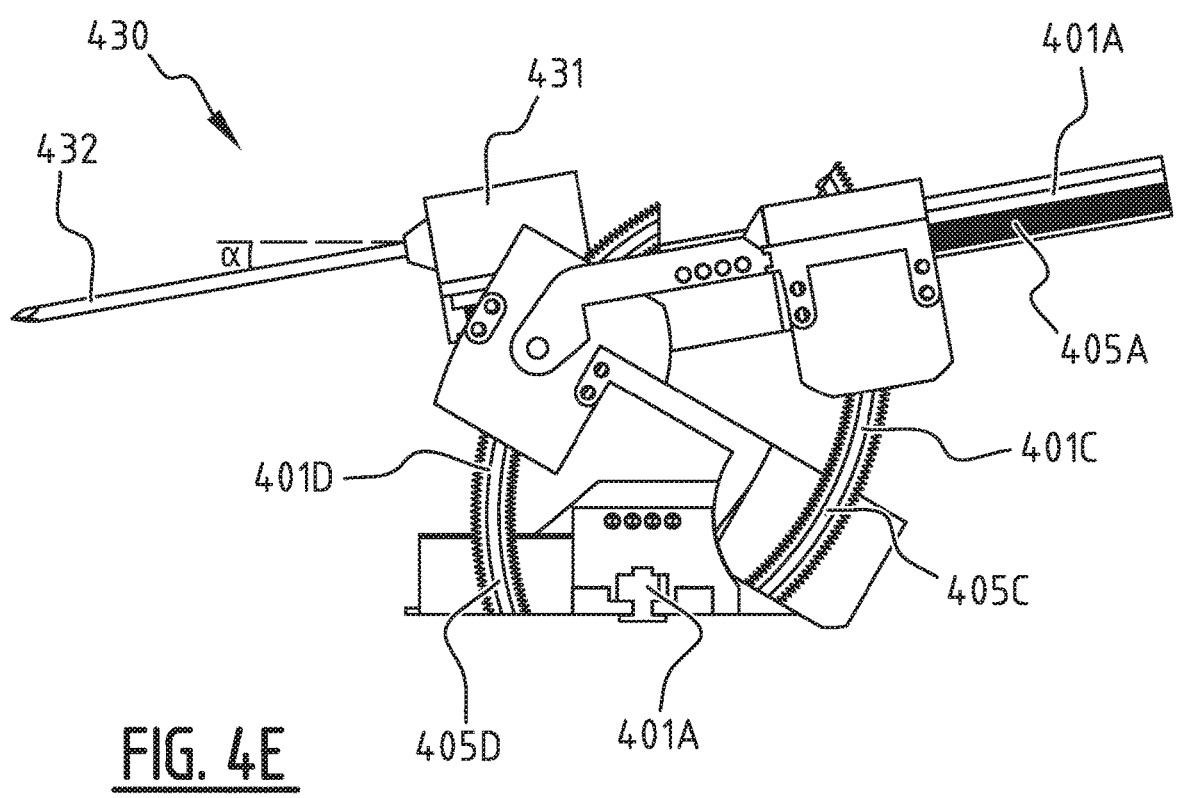

The invention will be further elucidated with reference to figures shown in a drawing and tables, wherein:

FIGS. 1A-1D schematically show a pneumatic stepper motor according to a first embodiment of the invention, wherein FIG. 1A is a perspective view, FIG. 1B is a side view, FIG. 1C is a horizontal cross section through the side view of FIG. 1B, and FIG. 1D shows a piston of the pneumatic stepper motor in a perspective view;

FIG. 2 schematically shows a horizontal cross section through a pneumatic stepper motor according to a second embodiment of the invention;

FIGS. 3A-3D schematically show a pneumatic stepper motor according to a third embodiment of the invention, wherein FIG. 3A is a perspective view, FIG. 3B is a side view, FIG. 3C is a horizontal cross section through the side view of FIG. 3B, and FIG. 3D shows the pistons and geared axle of the pneumatic stepper motor in a perspective view;

FIGS. 4A-4E schematically show a device according to a first embodiment of the invention, wherein FIG. 4A is a perspective back view, FIG. 4B is a perspective front view, FIG. 4C is a side view, and FIGS. 4D and 4E are the side view of FIG. 4C in a different position;

FIGS. 5-22 are figures relating to various pneumatic stepper motors that were designed, developed and tested;

FIG. 23 lists a number of MRI-compatible pneumatic stepper motors found in literature;

FIGS. 24-28 are tables relating to the various pneumatic stepper motors that were designed, developed and tested.

In the figures similar elements are denoted by similar reference numerals, increased by 100.

All references to directions and orientations, such as bottom, top, side, horizontal, vertical are in a normal use of the pneumatic stepper motor or device comprising the pneumatic stepper motor.

FIGS. 1A-1D show a linear pneumatic stepper motor 101, comprising in this example a housing with a first part 102 and second part 103, which first part 102 and second part 103 are connected to each other by means of screws that are inserted in screw bores 104 and are sealed by a sealant. It is noted that instead of screws any suitable connecting means, such as glue, may be used. An elongated, substantially straight rack 105 is partly accommodated in said housing and extends in a substantially horizontal, longitudinal direction there trough. Said rack 105 comprises gear elements 106 at two opposing longitudinal sides thereof, as is best shown in FIG. 1C. The first part 102 of the housing comprises two chambers 107, each accommodating one of two pistons 108. The pistons 108, see also FIG. 1D, each comprise two opposing engagement surfaces, wherein each engagement surface comprises a plurality, in this example five, first teeth 109 that extend in the direction of the rack 105. The gear elements 106 of the rack 105 in this example are formed by second teeth that can cooperate with the first teeth 109 of the pistons 108. Pneumatic tubes (not shown) can be connected to pneumatic tube sockets 110, such that air can be supplied to each of two longitudinal ends of each chamber 107, i.e. to in total four longitudinal ends. In use air is supplied via a said pneumatic tube to one longitudinal end at a time in order to drive a respective piston 108 in the direction of the other longitudinal end of that chamber 107. Any air optionally present in the other longitudinal end is pressed out of that other longitudinal end by said piston 108. With use of said air said pistons 108 are thus driven in a reciprocating movement between the two longitudinal ends of the chamber 107, wherein the reciprocating movement is in a substantially horizontal direction and in a direction substantially orthogonal to the longitudinal direction of the rack 105. Because the pistons 108 have first teeth 109 at the two opposing engagement surfaces thereof, each piston 108 will engage with the second teeth 106 of the rack 105 in both reciprocating movement directions thereof. In a first reciprocating movement direction one engagement surface with first teeth 109 will engage with the rack 105, and in the second, opposite reciprocating movement direction the other engagement surface with first teeth 109 will engage with the rack 105. As a result of the first teeth 109 engaging with second teeth 106, a relative displacement between the piston 108 and rack 105, and therefore between the rack 105 and housing, is obtained, such that the rack 105 and housing are able to be moved with respect to each other in the longitudinal direction of the rack 105. Practically said rack 105 may be a fixed rack, such that said housing may be moved along the rack 105, but it may also be the case that said housing is fixed and that said rack 105 is moveable.

The four engagement surfaces with first teeth 109 of the two pistons 108 are driven in an off phase manner with respect to each other and the rack 105, such that at a certain time only one engagement surface fully engages with the rack 105. In FIG. 1C, the first teeth 109 of one engagement surface of the left piston 108 fully engage with the second teeth 106 of one longitudinal side of rack 105, i.e. the first teeth 109 accommodated in longitudinal end 114 of the left chamber 107, and the first teeth 109 of the other, opposing engagement surface are at a distance from the second teeth of the other longitudinal side of rack 105, i.e. the first teeth 109 accommodated in longitudinal end 113 of the left chamber 107. In FIG. 1C air supply to one longitudinal end 111 of the right chamber 107 has just started, such that the right piston 108 has just started to move in the direction of the other longitudinal end 112 of that chamber 107. The first teeth 109 of the engagement surface accommodated in said one longitudinal end 111 have just contacted the second teeth 106 of the rack 105. Upon further movement of the piston 108 in the direction of the other longitudinal end 112 of that chamber 107, the first teeth 109 will slide along the inclined surface of the second teeth 106 of the rack 105, such that the housing and rack 105 are moved with respect to each other in the longitudinal direction of the rack 105 until the first teeth 109 and second teeth 106 fully engage. Next, air may be supplied to again another longitudinal end of a different chamber 107, preferably to the longitudinal end 113 of the left chamber 107, such that the left piston 108 is moved in the direction of the longitudinal end 114, such that the housing and rack 105 are moved with respect to each other in the same longitudinal direction of the rack 105. If air is supplied to the four longitudinal ends of the two chambers 107 in a suitable sequence, the housing and rack 105 may thus be moved with respect to each other in a first direction in the longitudinal direction of the rack 105, and if the sequence is reversed the housing and rack 105 may thus be moved with respect to other in a second, opposite direction in the longitudinal direction of the rack 105. Said sequence is preferably 114-111-113-112 and said reversed sequence is 112-113-111-114. A controller, for example a pneumatic valve manifold, may be provided in order to control the air supply and in particular the sequence thereof. As is best visible in FIG. 1C, the second teeth 106 of the two longitudinal sides of the rack 105 are shifted with respect to each other over 180 degrees, such that a valley between two second teeth 106 of one longitudinal side is opposite to a tip of a second tooth 106 of the other longitudinal side. Further, there is a phase shift of 90 degrees between the second teeth 106 at one longitudinal side of the rack 105 and the two engagement surfaces of the two pistons 108 on that one longitudinal side of the rack 105. As such, there is a phase shift of 90 degrees between each engagement surface and the rack 105.

As is best shown in FIG. 1C, each piston 108 comprises two seals 115, wherein each seal is arranged on a side of the piston 108 that is opposite to the engagement surface from which the first teeth 109 extend, i.e. said seals are directed towards the longitudinal ends of the chambers 107 and/or towards the air supply by the pneumatic tubes.

As is best shown in FIG. 1D, in this example said piston 108 comprises a plate like element 116 that extends between and mutually connects the two engagement surfaces comprising said first teeth 109 and thus extends between the first teeth 109 of each engagement surface. Said plate like element 116 defines a bottom surface of a cavity 117, said cavity 117 being arranged for accommodating said rack 105.

FIG. 2 shows a second embodiment of a pneumatic stepper motor 201 according to the invention, in this case a curved stepper motor. Only the differences with respect to the pneumatic stepper motor 101 of the first embodiment shown in FIGS. 1A-1D will be described here. For a further description the reader is referred to the description of FIGS. 1A-1D.

The pneumatic stepper motor 201 according to the second embodiment comprises an elongated, substantially curved rack 205 that is partly accommodated in the housing (only the first part 202 of the housing is shown in FIG. 2) and extends in a substantially horizontal, substantially curved longitudinal direction there through. The second teeth 206 are provided at two opposing, curved longitudinal sides of the rack 205. The chambers 207 in which the pistons 208 are accommodated extend substantially orthogonal to a local longitudinal axis or direction of the curved rack 205, i.e. the longitudinal direction between the longitudinal ends 211-214 of the chambers 207 is substantially orthogonal to a local longitudinal axis L or direction of the curved rack 205. In this example, the engagement surfaces of the pistons 208 directed towards the convex side of the rack 205 comprise ten first teeth 209, and the engagement surfaces of the pistons 208 directed towards the concave side of the rack 205 comprise twelve first teeth 209. The first teeth 209 directed towards the concave side of the rack 205 are smaller than the first teeth 209 directed towards the convex side of the rack 205. The second teeth 206 provided at the concave longitudinal side of the rack 205 are smaller than the second teeth 206 provided at the convex side of the rack 205. It is thus clear that, if said rack 205 is curved, the size and/or number of the first teeth 209 and/or the size of the second teeth 206 may differ for the concave and convex side of the rack 205, and in particular the size of the first and second teeth 209, 206 may be smaller and/or the number of first teeth 209 may be higher for the concave side of the rack 205 in comparison to the convex side of the rack 205. This is because the curved longitudinal translation of the pistons 208 with respect to the rack 205 is larger for the convex side of the rack 205 than for the concave side of the rack 205.

It is noted that for the sake of simplicity the pneumatic tube sockets are not shown in FIG. 2. No screw bores are shown because in this second embodiment the two housing parts may be glued to each other.

FIGS. 3A-3D show a third embodiment of a pneumatic stepper motor 301 according to the invention. Only the differences with respect to the pneumatic stepper motor 101 of the first embodiment shown in FIGS. 1A-1D will be described here. For a further description the reader is referred to the description of FIGS. 1A-1D.

FIGS. 3A-3D show a rotational pneumatic stepper motor 301, comprising a geared axle 305. The second teeth 306 extend substantially radial with respect to a longitudinal axis 318 of the geared axle 305 and are evenly distributed over the circumference thereof. In this example, nine second teeth 306 are provided, wherein a pitch angular distance between neighbouring second teeth 306 is thus approximately 40 degrees. Each engagement surface of the two pistons 308 comprises in this example three first teeth 309. The chambers 307 in which the pistons 308 are accommodated extend substantially orthogonal to the longitudinal axis 318 of the geared axle 305, i.e. the longitudinal direction between the longitudinal ends 311-314 of the chambers 307 is substantially orthogonal to the longitudinal axis 318 of the geared axle 305. In this example, the pneumatic tube sockets 310 are located in the sides of the housing, i.e. the circumference thereof. As a result of a reciprocating movement of the two pistons 308 by supplying air to the longitudinal ends of the chambers 307 in a sequence of 314-311-313-312, the housing and geared axle 305 are moved in a rotational movement with respect to each other in a first rotational direction, and in a reversed sequence of 312-313-311-314, the housing and geared axle 305 are moved in a rotational movement with respect to each other in a second, opposite rotational direction.

FIGS. 4A-4E show a device 430 according to a first embodiment of the invention. The device of FIGS. 4A-4E is an MRI-guided breast biopsy device. The device 430 comprises in total four pneumatic stepper motors, namely two linear pneumatic stepper motors 401A, 401B that are similar in function to the one shown in FIGS. 1A-1D, and two curved pneumatic stepper motors 401C, 401D that are similar in function to the one shown in FIG. 2. For a description on how the pneumatic stepper motors 401A-401D function, the reader is therefore referred to the description of FIGS. 1A-1D and 2.

The four pneumatic stepper motors 401A-401D are arranged to move a needle 432 that is held by a needle holder 431 in four degrees of freedom.

The two curved pneumatic stepper motors 401C, 401D each have a curved rack 405C, 405D which curved racks 405C, 405D are arranged substantially vertical, i.e. the curved longitudinal directions thereof are substantial vertical in use of the device, and with the concave parts thereof directed towards each other. The needle holder 431 is connected to the racks 405C and 405D via respective housings 402C, 403C and 402D, 403D, which housings 402C, 403C and 402D, 403D are able to be moved independently with respect to each other along the curved longitudinal direction of the curved racks 405C, 405D as a result of the reciprocating movements of the two pistons accommodated in the chambers therein. The needle holder 431 can thus be lifted and lowered in an upward, respectively downward direction along said curved racks 405C, 405D, wherein FIG. 4C shows the lowest position of the needle holder 431 and FIGS. 4D and 4E show the needle holder in a higher position. In addition, the needle holder 431 can be tilted with respect to the horizontal, wherein FIG. 4D shows the needle 432 having a positive angle $\alpha$ with respect to the horizontal, and FIG. 4E shows the needle 432 having a negative angle $\alpha$ with respect to the horizontal. FIG. 4C shows the needle 432 being parallel to the horizontal. Tilting of the needle occurs when the housings 402C, 403C and 402D, 403D are at a different height position along the curved racks 405C and 405D.

The two linear stepper motors 401A, 401B each have a straight rack 405A, 405B.

The rack 405A is arranged substantially horizontal and the longitudinal direction thereof is substantially orthogonal to the longitudinal direction of the needle 432, at least in a rest position of the needle 432 shown in FIG. 4C. A housing 402A, 403A, to which the needle holder 431 is connected, is able to move along rack 405A, such that the needle holder can be moved sidewards, i.e. orthogonal with respect to the longitudinal direction of the needle 431. Said housing 402A, 403A remains substantially horizontal and cannot be moved upwards or tilted. Said housing 402A, 403A is said predetermined part of the claims.

The longitudinal direction of the rack 405B is substantially parallel to the longitudinal direction of the needle 432, and the rack 405B can be lifted, lowered and tilted together with the needle holder 431 along the curved racks 405C, 405D. The needle holder 431 is connected to and able to move along the rack 405B via a housing 402B, 403B, such that said that said needle holder 431 and thereby the needle 431 is able to be moved substantially forwards and backwards in order to be able to puncture and retract from a breast during use of the device.

It is noted that for example said linear stepper motor 401A may be interchanged for a curved stepper motor with a curved rack, wherein the concave side of the curved rack is preferably directed towards the breast in use of the device, such that the predetermined part is able to be moved around said breast in a substantially horizontal direction.

In the following it is described how various pneumatic stepper motors were designed, developed and tested. This description is included to provide some detailed background information on the pneumatic stepper motors that were designed, developed and tested, but is not intended to be limiting in any way. Any of the below described features, advantages or other characteristics may be part of the invention, alone or in combination.

Five pneumatically-driven linear and rotational stepper motors have been developed, with forces up to 330 N, torques up to 3.7 Nm, stepping frequency up to 320 Hz, dimensions ranging from 25 mm to 80 mm and power up to 26 W. All five motors can be constructed from six 3D printed parts and four hand-cut (or laser-cut) seals, held together by nylon screws or clips. The described stepper motors outperform state-of-the-art plastic pneumatic stepper motor designs, both in specifications and in manufacturability. All of them are designed according the same design principles. The main challenges here are in designing space-efficient cylinders that have large bores (for high forces) and are well sealed (to avoid leakages), and in transferring the piston force to the rack or gear. Classic cylindrical-shaped pneumatic cylinders with protruding rods are difficult to rapid prototype, so a different method is used that essentially involves placing the rack or gear right through the pistons themselves, as employed earlier in laser-cut pneumatics. This eliminates the need of a protruding rod, greatly simplifying the design. Another design choice is the use of rectangular-shaped cylinders, to maximize rapid prototypeability.

Figure 5A:
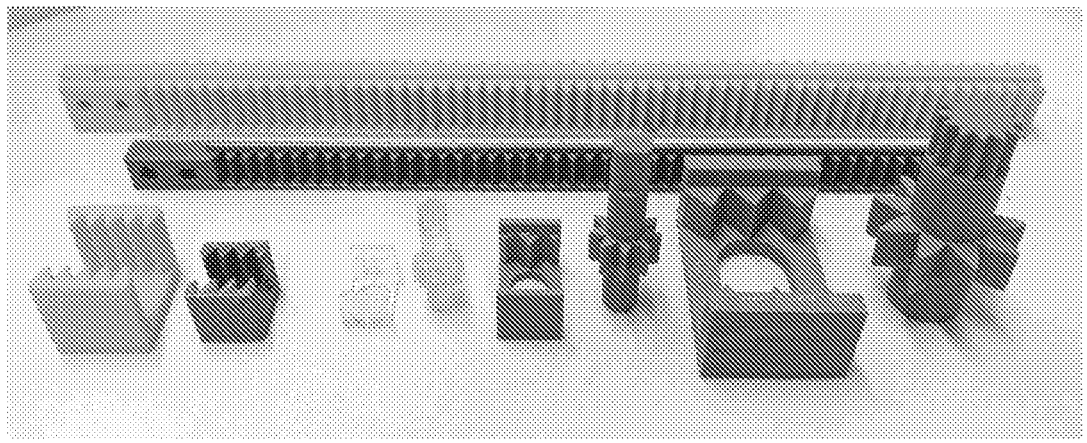
Figure 5B:
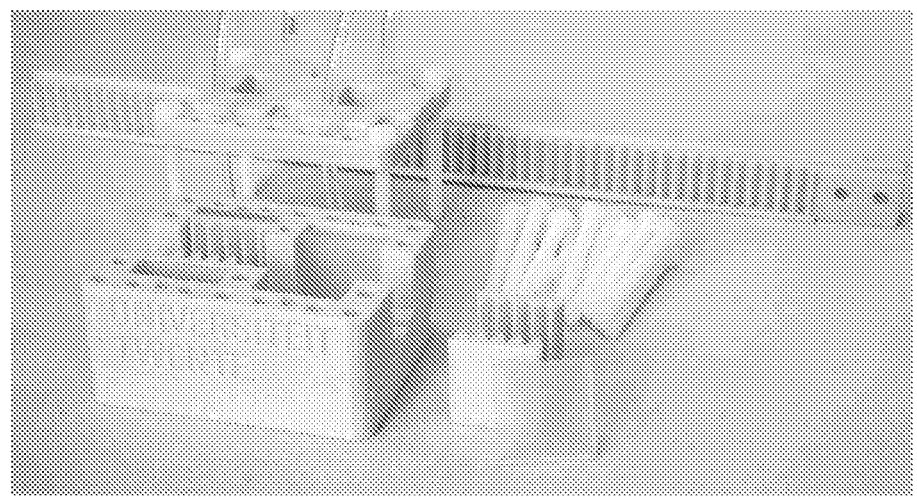

All five motors consist of six different custom components: the housing with top and bottom cover, two identical toothed pistons, four identical silicone seals and one rack or geared axle. FIGS. 5A and 5B show racks, gears and pistons of the different motors; it can be seen that the pistons are box-shaped with a cut-out space in its center, and series of teeth facing this cut-out space. Except for the R-25, the housing parts are held together with M4 nylon screws and sealed by blue silicone (Loctite 5926).

The box-shaped pistons are sealed by rectangular silicone rubber seals with slanted edges that are hand-cut from 2 mm silicone rubber using a 3D printed cutting guide. For the R-25 motor, the seals were laser-cut after engraving to a depth of 1 mm along the border to obtain the right shape.

Gears and racks have one actuated degree of freedom, all other motions are kinematically constrained by holes for the axles and linear guide rails for the racks. Polyurethane tubing is either mechanically clamped, or glued (with Loctite 770 primer+Loctite 406 glue) into the housing, with air vents leading to each chamber. The housing is made airtight by applying a very dilute solution of transparent ABS in acetone to its walls.

By pressurizing a chamber, the piston is pushed to the other end, engaging the rack or gear enclosed by the piston's jaws. The teeth of the piston interact with the teeth of the rack or gear according to the wedge principle, resulting in step-wise translational or rotational movement. Each motor contains two pistons, with a total of four jaws combined, phased 90° apart. Using just one piston would not allow bidirectional travel; using three or more pistons does not give additional value except when back-driveability is a requirement.

Except for the silicone seals and nylon screws, all parts of the T-63 and T-49 motors are 3D printed with the Ultimaker 2 in PLA with 0.1 or 0.2 mm layer height. The T-44 motor also uses ABSplus material printed with the Stratasys uPrint SE machine for higher temperature resistance, while the T-25 motor is produced with an Objet 250Eden printer in FullCure720 material. Printing generally takes around ten hours, while assembly can be performed in less than one hour. FIGS. 5A and 5B show a couple of pistons, racks and gears. Parts are printed solid and single walled, for maximum strength. Walls surrounding the rectangular cylinder bores are at least 7 mm thick to resist deformation under pressure, as the bore's cross-sectional shape is rectangular and not circular. From FEM simulations, thin walls may deform under pressure by more than 0.1 mm at a pressure of 0.4 MPa, and from experiments it is known that such deflections result in excessive air leakage.

The Ultimaker 2 and Stratasys uPrint SE produce parts using fused filament fabrication, a very popular and relatively low-cost 3D printing technique. The resulting parts are not isotropic, which implies that actual shear strength depends on the orientation of the shear plane. Also, surface roughness varies significantly: of the bottom-facing faces, in the Ultimaker 2 the lowermost one is smooth because it is printed directly on the glass print bed, while all other bottom-facing faces are rough. The top-facing faces are moderately rough, but the topmost one can be easily polished smooth by grinding. The side faces are all grooved due to the layered printing technique. For moving parts to slide with minimal friction, surfaces have to "match" in smoothness: moderately rough surfaces must be coupled with smooth ones, and grooved surfaces must slide in the direction of the grooves. A lubricant such as petroleum jelly can be used to reduce the friction further.

Figure 6A:
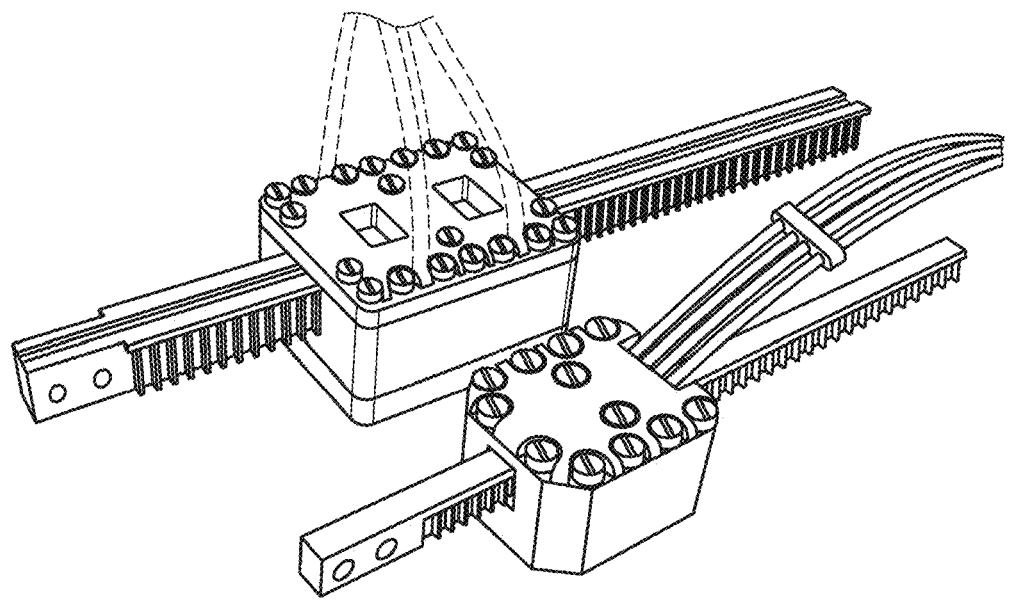
Figure 7A:
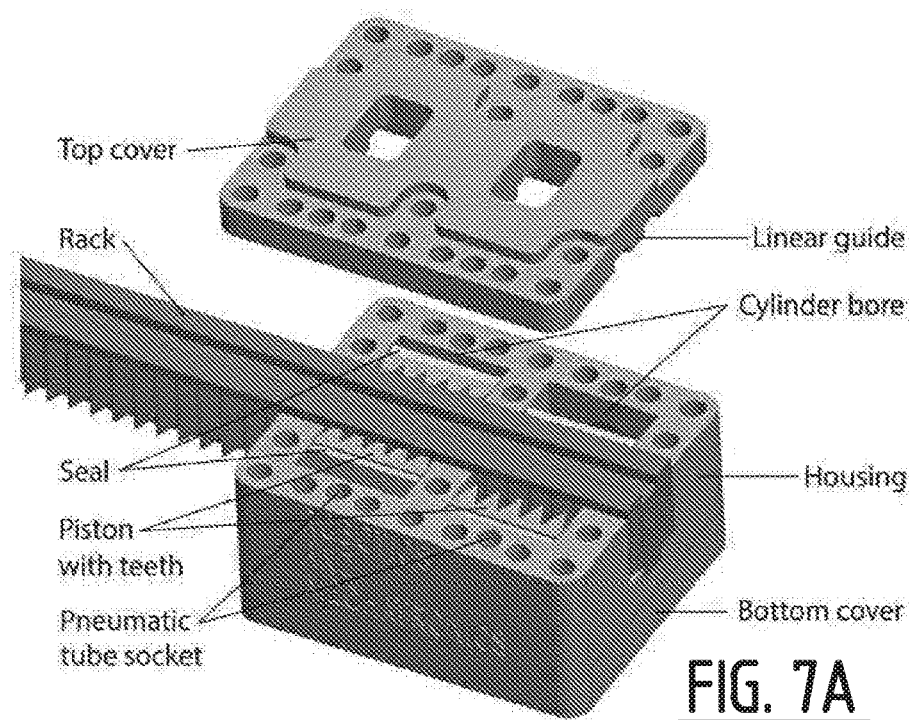
Figure 7B:
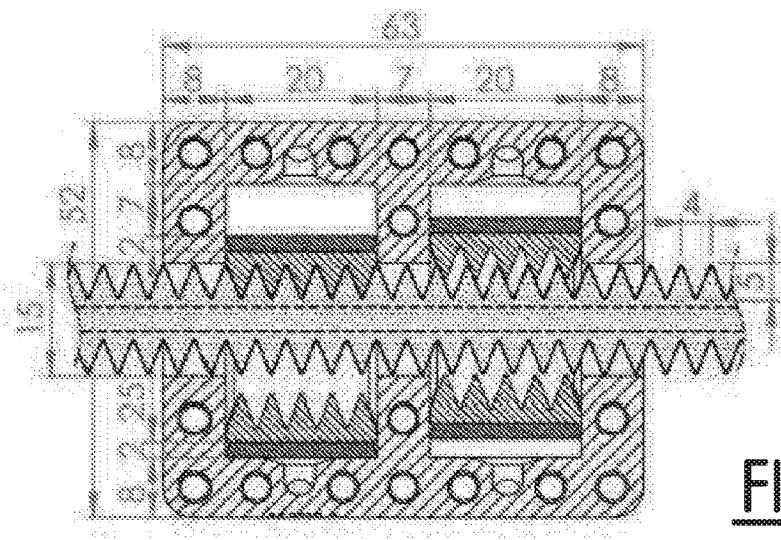
Figure 7C:
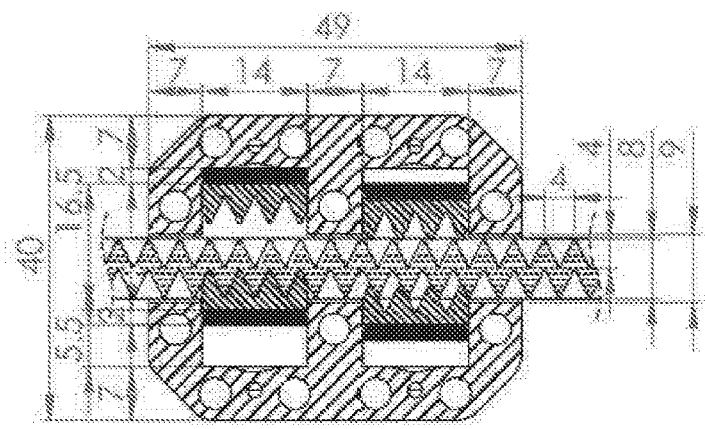
Figure 8A:
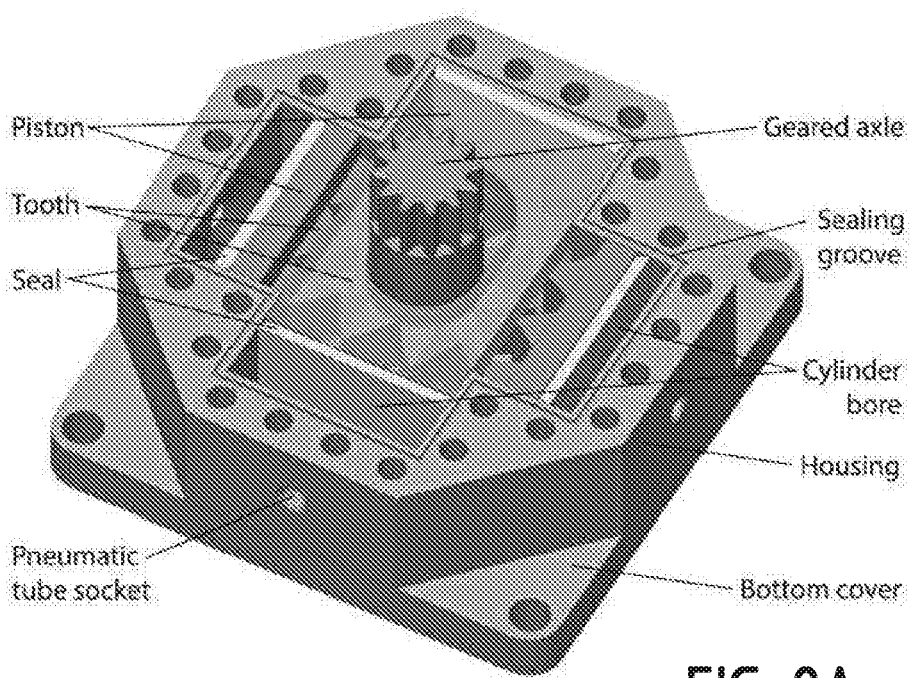
Figure 8B:
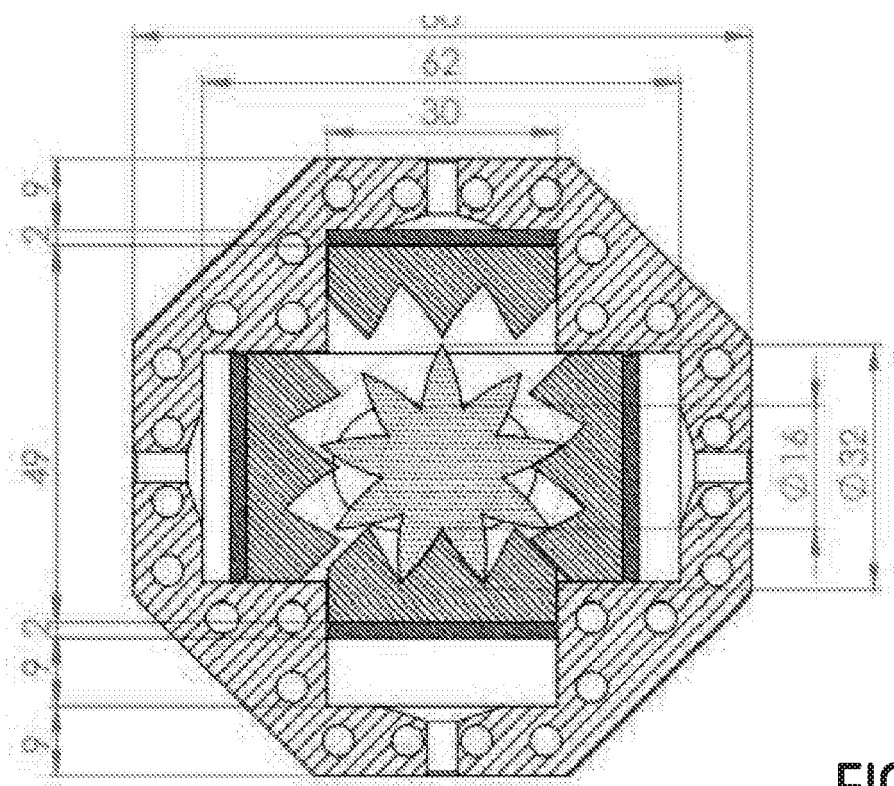
Figure 8C:
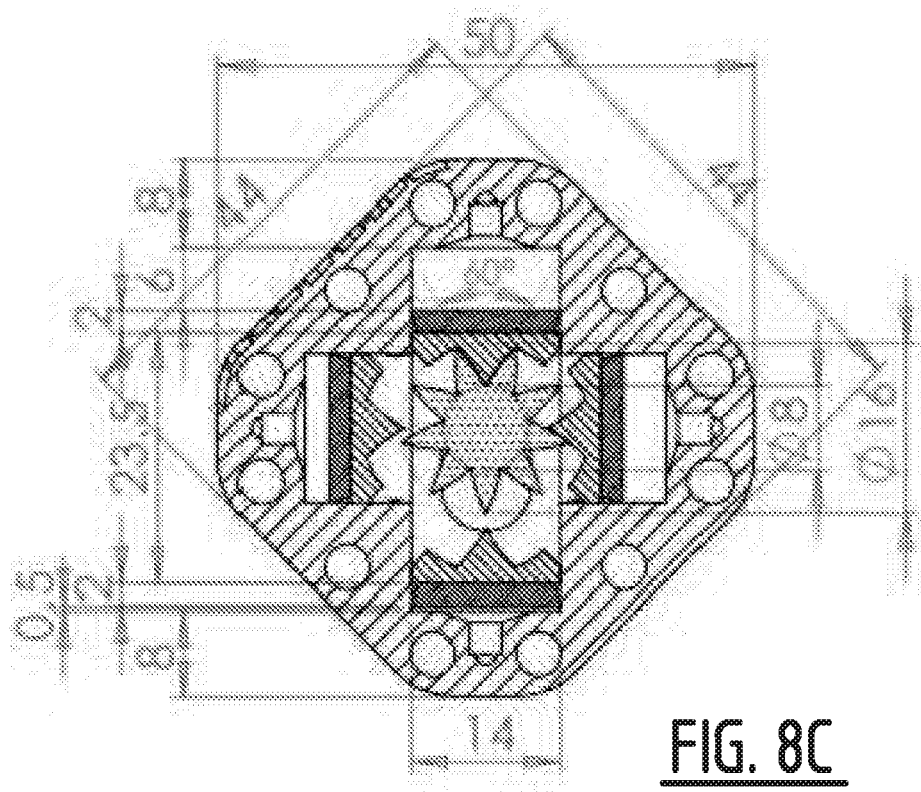
Figure 8D:
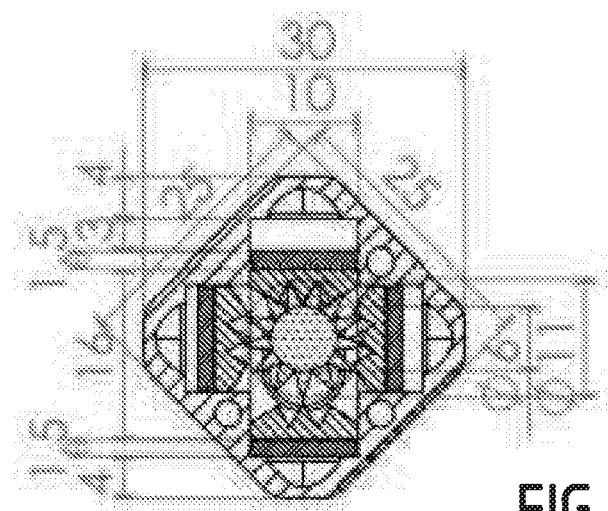

The T-63 motor, see FIG. 6A (top), is a linear motor with dimensions 63×52×36 mm. FIGS. 7A and 7B show CAD drawings of the motor, and FIG. 5B shows a picture of a partially assembled motor, exposing its components. 4 mm tubes are mechanically clamped by purposedly misaligning the pneumatic tube socket holes in the top and middle housing parts. The teeth pitch is 4 mm and depth is 5 mm, resulting in a teeth tip angle of 43.6°. Smaller tip angles would make the teeth structurally weak, while larger angles are less effective in transferring forces from piston to rack. Narrower pitch sizes are too difficult to print with accurate detail using a 0.4 mm extruder, and larger pitch sizes are more appropriate for large scale applications.

The bore's cross-sectional area is 20 mm×20 mm×400 mm². When supplied with a pressure P, a force $F_p=P·A=4·10^{-4}·P$ is exerted on the piston. The teeth act on the rack by means of a wedge mechanism. A piston displacement of 2.5 mm results in 1 mm rack displacement, so the wedge factor is $\alpha=2.5/1=2.5$ and the force transferred from piston to the rack is increased by this factor. Ignoring friction, the output force F satisfies $F_r=\alpha F_p=10^{-3}·P$. At a pressure of P=0.3 MPa, the output force will then be $F_r=300$ N. The actual output force is less due to friction losses between moving parts (seals, pistons, rack) which can be determined experimentally.

The T-49 motor is a miniaturized version of the T-63 motor. See FIG. 7C for the cross-sectional drawing and FIG. 6A (bottom) for the realization. The bore size is decreased to 14×14 mm=196 mm², approximately half the area of the T-63. While the teeth pitch stays the same (4 mm), the teeth depth is reduced from 5 mm to 4 mm for compactness, resulting in a wedge factor of $\alpha=2.0$. The rack is narrowed from 15 mm to to 8 mm in width, by making more efficient use of the available space. The four 3 mm pneumatic tubes are arranged adjacently to each other to save space around the motor; pressurized air is guided to the pistons through internal channels in the top cover of the housing. When pressurized with a pressure of P, the force exerted by the rack (ignoring friction losses) is $F_r=\alpha·P·A=4·10^{-4}·P$. At 0.3 MPa pressure, the theoretical force is 120 N.

The R-80 is a rotational stepper motor. See FIGS. 8A and 8B for the CAD designs and FIG. 6B (left) for the realization. Laser-cut 8 mm acrylic plates are used for top and bottom covers for better visibility of the internal mechanics. The housing was 3D printed in ABS and the pistons and geared axle were 3D printed in PLA. The two pistons act on a gear to rotate it around, requiring the piston movement to be perpendicular to the gear tip's motion profile. Therefore, the two identical pistons have to be placed in a cross configuration, embracing the axle, and the pistons have a slotted hole for the axle.

Dimensions are 80×80×37 mm and the bore size is 30×20 mm=600 mm², resulting in 60 N of force per 0.1 MPa pressure. The gear has nine teeth, with circular pitch 40° and teeth depth 8 mm. The step size is 10°, equal to one quarter of the circular pitch. Upon a piston movement of x=4 mm, the gear rotates by $\beta=10°$. The torque T as function of pressure P can be found using the work balance $T\beta=Fx=PAx$, so:

$$T = P\frac{6 \cdot 10^{-4} \cdot 4 \cdot 10^{-3}}{10 \cdot \pi/180} \approx 1.38 \cdot 10^{-5} P.$$

For a pressure of 0.3 MPa, the theoretical output torque (ignoring friction losses) is thus 4.1 Nm.

Ideally, the piston teeth surface keeps maximal contact with the gear when sliding on it. However, unlike in the linear stepper motor designs, there is no mathematically perfect solution for the shape of the planar contact curve. Curved segments that keep full contact when sliding, must be circular or straight. But if the angle between the tangent and radial line is to be kept constant, the curve must be a logarithmic spiral which does not have a constant radius of curvature. The consequence is that the piston and rack have a much smaller effective contact surface area than in linear stepper motors.

The R-44 is a miniaturized version of the R-80 rotational motor. The cross-sectional drawing is in FIG. 8C and the realization is in FIG. 6B (middle). By making efficient use of the available space, the R-44 occupies a quarter of R-80's volume. The pistons and geared axle are made out of ABSplus material because of the higher heat deflection temperature of 96°, compared to 60° of PLA. This is essential because the small parts heat up quickly due to friction, when operating at high speeds. The 3 mm pneumatic tubes are bundled and routed through the bottom cover, analogous to the T-49 design. The bore dimensions are 14×14 mm=196 mm². The gear counts nine teeth with depth 4 mm. The theoretical torque T (ignoring friction losses) as function of input pressure P is $$T = P\frac{2 \cdot 10^{-3} \cdot 2 \cdot 10^{-4}}{10 \cdot \pi/180} \approx 2.29 \cdot 10^{-6} P.$$

For a pressure of 0.3 MPa, the theoretical output torque is thus 0.69 Nm, which is one-sixth of that of the R-80.

Figure 6B:
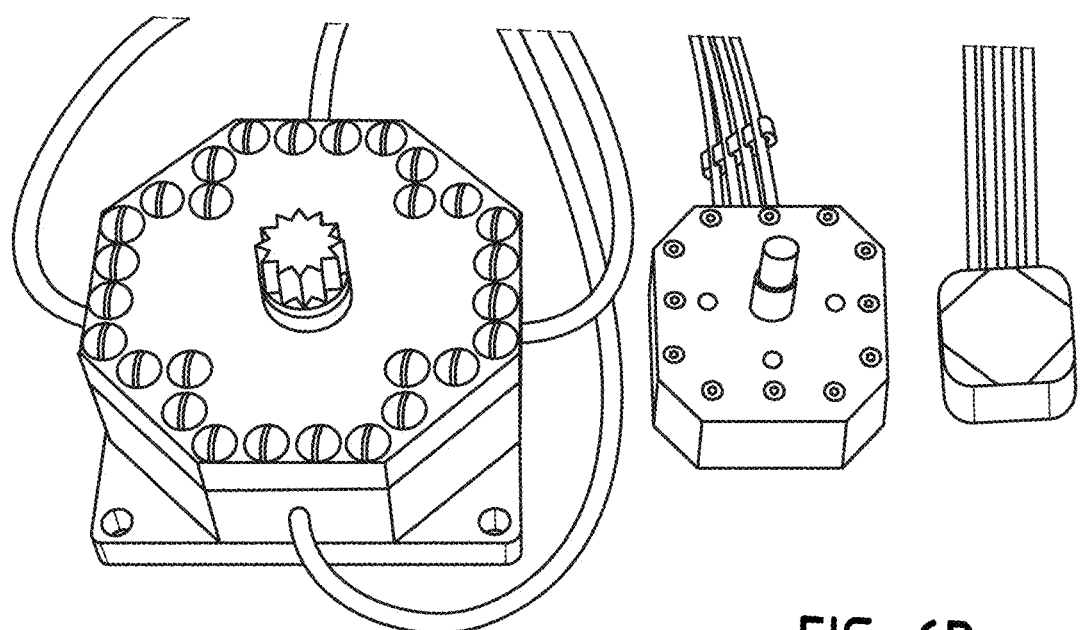

The R-25 motor, see FIG. 6B (right) is a further miniaturized version of the R-80 and R-44. See FIG. 8D for the cross-sectional drawing. The dimensions are 25×25×20 mm and it is produced with the Stratasys Objet Eden250 in Fullcure720 material. The housing consists of two parts, held together by clips that are laser-cut from PET material. The bore dimensions are 10×10 mm=100 mm². The gear counts thirteen teeth with depth 2.5 mm. The theoretical torque T (ignoring friction losses) as function of input pressure P is $$T = P\frac{4 \cdot 13 \cdot 1 \cdot 10^{-4} \cdot 1.25 \cdot 10^{-3}}{2\pi} \approx 1.03.$$

$10^{-6}$P. For a pressure of 0.3 MPa, the theoretical output torque is thus 0.31 Nm, roughly half of R-44's torque.

To obtain performance characteristics of the motors, various measurements were performed.

Figure 9:
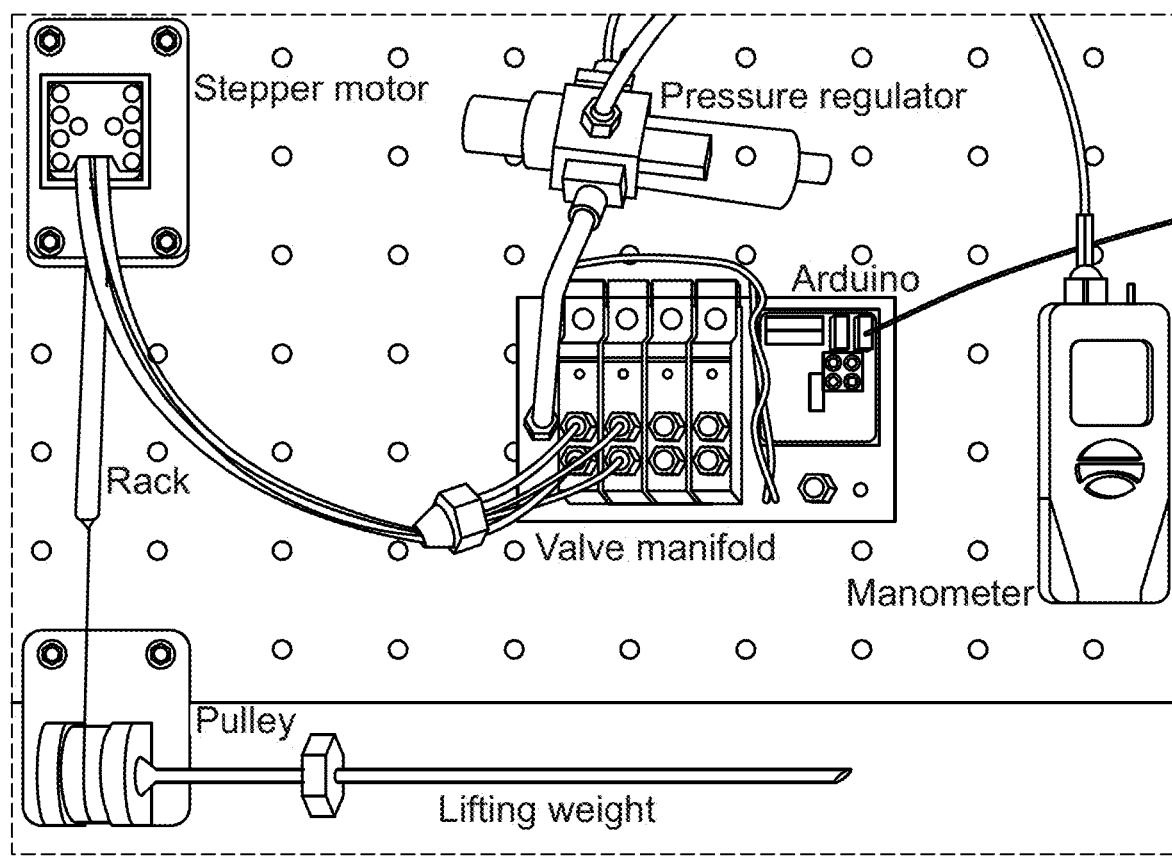

FIG. 9 shows the basic measurement setup. Constant force loads on linear stepper motors were generated by lifting combinations of weights of known mass using a pulley. Winches with radius 20 mm or 50 mm allow to convert these forces to torques to load rotational stepper motors. The system pressure is adjusted using a manual pressure regulator and measured with a digital pressure meter. The stepping frequency is controlled by an analog turn knob connected to the Arduino controller of the valve manifold, its frequency setting is communicated over a serial interface to a laptop and displayed on its screen. Acceleration is kept within safe margins. The Arduino keeps an internal step counter and allows to define two preset positions for feedforward position control. The directly actuated valves are of type Festo MHP2-MS1H-5/2-M5, with average response time of 1.8 ms and nominal flow rate of 100 L/min.

Measurements were performed to investigate the relation between force/torque, pressure, stepping frequency and tube length. The following measurements were conducted:

Force/torque versus pressure (all motors): The weight is varied and the pressure is adjusted to the lowest level where the motor can just lift the given weight without missing steps, at low frequency (around 1 Hz) and short tubes (0.20 m).

Maximum unloaded speed (all motors): Stepping frequency is increased until the motor misses steps. This can be observed by moving between two preset step count positions, and checking that the actual preset positions do not drift away. Short (0.20 m) tubing was used and pressure was adjusted such that the stepping frequency can be pushed as high as possible.

Force versus pressure at different stepping frequencies (T-49 only): The weight and stepping frequency are varied and the pressure is adjusted to the lowest level where the motor can just lift the given weight without missing steps, with short tubes (0.20 m). Only the T-49 motor was tested in this experiment.

Force versus speed for different tube lengths (T-49 only): The pressure is fixed at 0.55 MPa and the maximum stepping frequency was determined for all combinations of weight (0 N, 35 N, 70 N, 100 N) and tube length (0.20 m, 1.0 m, 5.0 m). Only the T-49 motor was tested in this experiment.

Maximum power (all motors): Possible combinations of stepping frequencies, weight load and pressure are investigated and tweaked to find the operating point of maximum power for the motor.

Figure 10A:
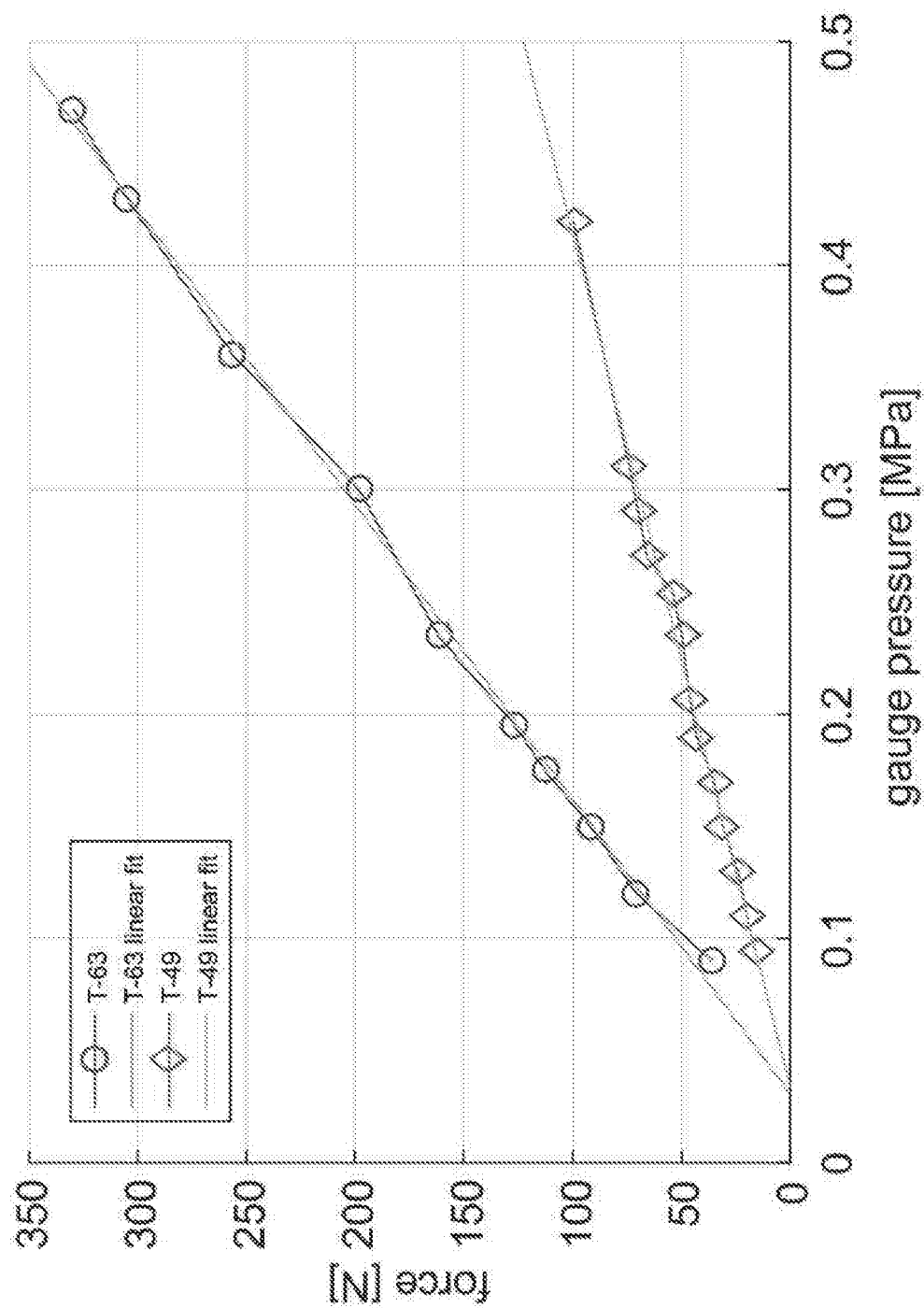

FIG. 10A gives the force characteristics of both linear stepper motor designs, and FIG. 24 the highest measured force or torque for each motor. The T-63 is capable of delivering 330 N of force, while the T-49 was tested up to 100 N. Both linear motors never broke down, which means that the maximum load could be even higher. As the force-pressure graphs are approximately linear, we can use linear fitting, giving the following characteristic equations (F in Newton, P in Pascal):

Linear fit for T-63:

$$F=7.6 \cdot 10^{-4}P-23$$

Linear fit for T-49:

$$F=2.6 \cdot 10^{-4}P-9.0$$

Comparing the slopes with the theoretical model, we see that the T-63 has an efficiency of $$\frac{7.6}{10} = 76\%.$$

This is the ratio or work performed by the rack, to work performed by the pressurized air in the cylinder. The remaining work is lost due to friction in sliding parts, and converted to heat. The T-49 has an efficiency of $$\frac{2.6}{4} = 65\%.$$

Comparing the slope ratios of the T-63 and T-49, we see that the T-63 motor is a factor $$\frac{7.6}{2.6} \approx 2.9$$

stronger than the T-49 motor.

Figure 10B:
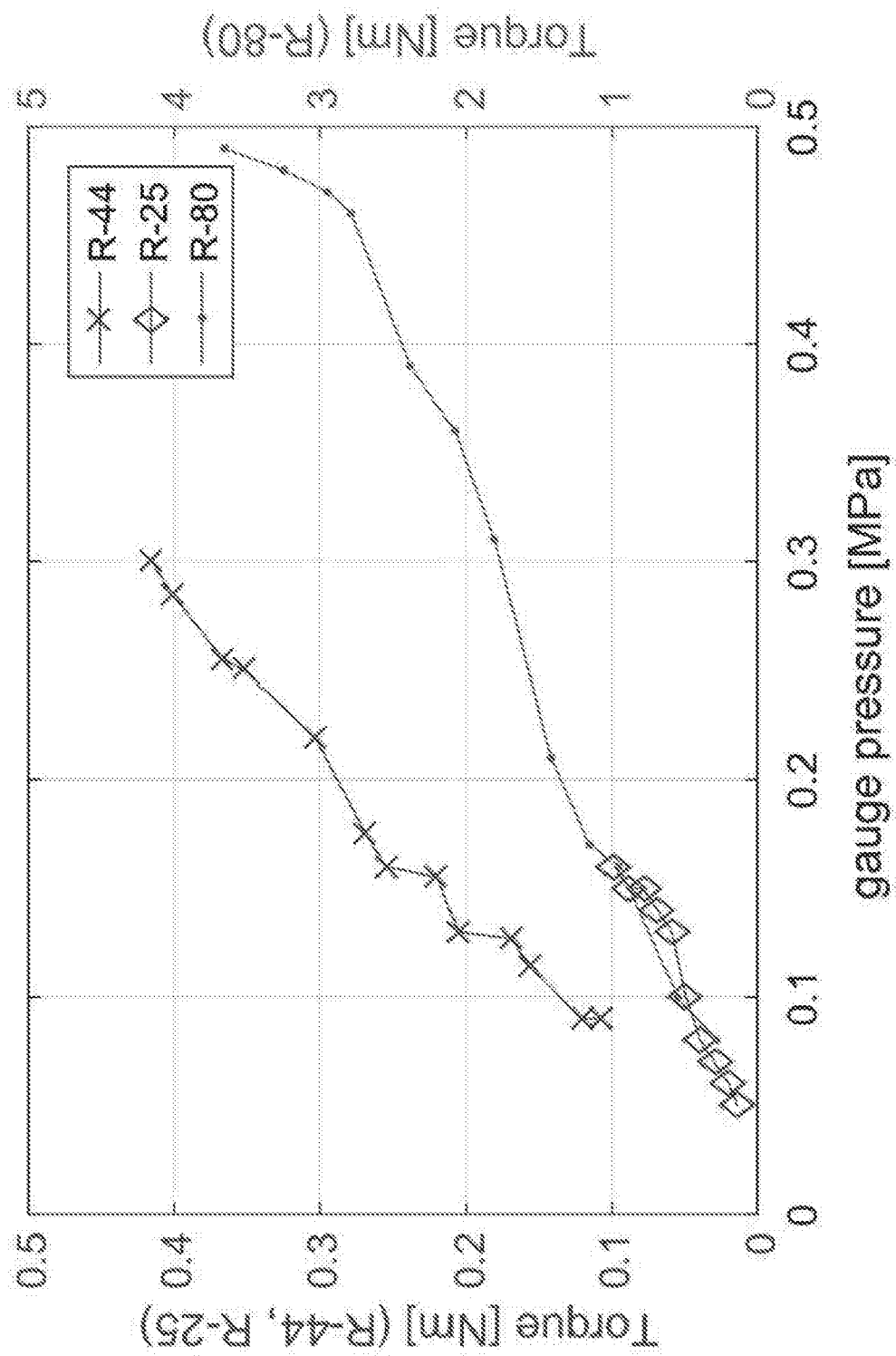

FIG. 10B gives the torque characteristics of the three rotational stepper motor designs. The R-80 is capable of exerting 3.7 Nm of torque, at a higher load one tooth broke off. The R-44 exerted over 0.48 Nm of torque before breaking down. The R-25 was tested up to 0.10 Nm, which is also close to its point of breakdown.

Again, all characteristic curves are approximately linear and the following linear fits were found:

Linear fit for R-80:

$$T=6.91 \cdot 10^{-6}P-0.18$$

Linear fit for R-44:

$$T=1.44 \cdot 10^{-6}P-0.00$$

Linear fit for R-25:

$$T=0.68 \cdot 10^{-6}P-0.02$$

The efficiency of the R-80

$$\frac{6.91 \cdot 10^{-6}}{1.38 \cdot 10^{-5}} = 50\%.$$

The efficiency of R-44 is $$\frac{1.44}{2.29} = 63\%$$

and R-25's efficiency is $$\frac{0.68}{1.03} = 66\%.$$

These values are also listed in FIG. 24.

The maximum unloaded stepping frequencies are listed in FIG. 25. The T-49 is the fastest with 320 steps/s, and R-80 the slowest with 80 steps/s.

Figure 11A:
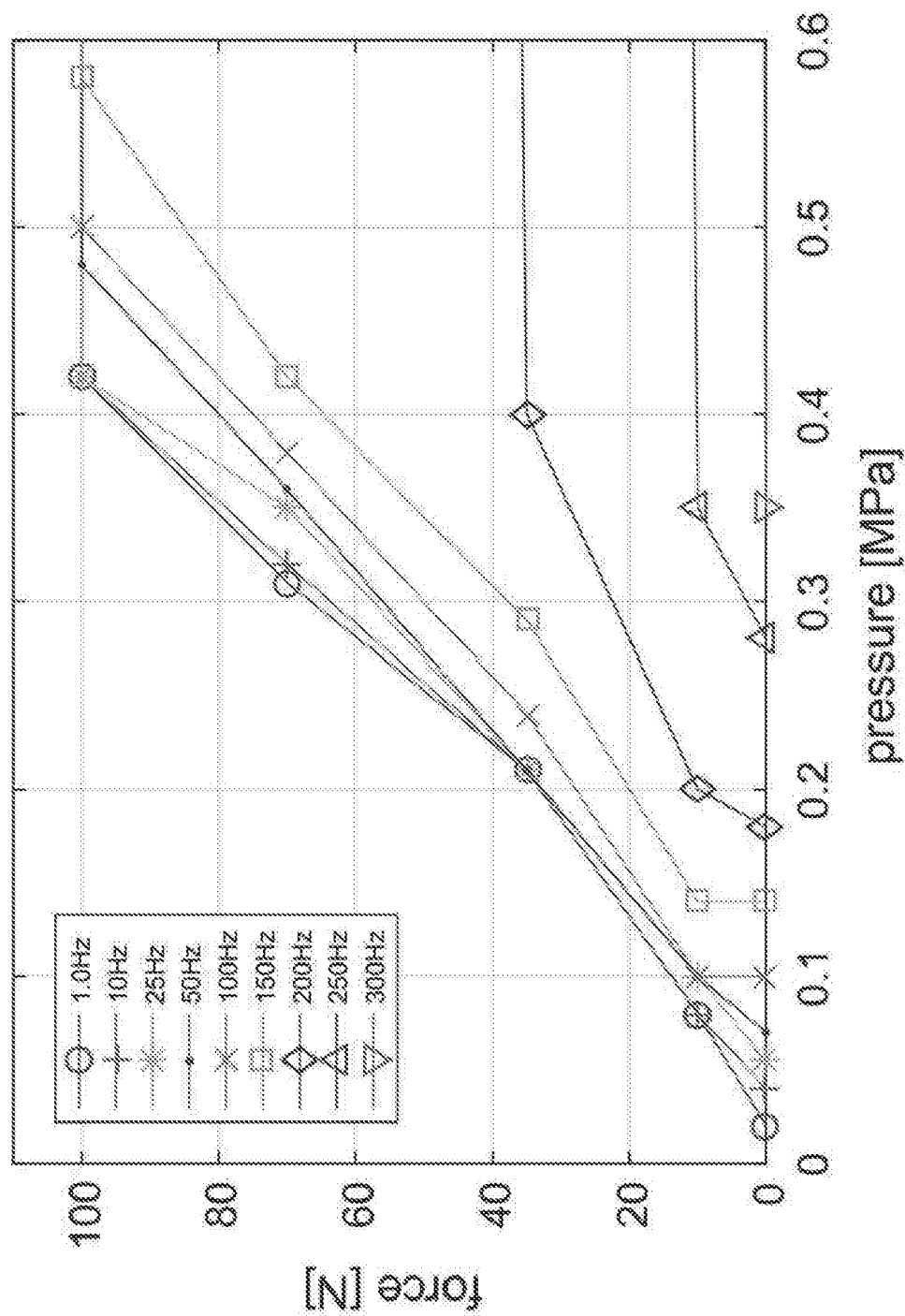

FIG. 11A shows the force/pressure relationship of the T-49 motor for different stepping speeds. At low speeds, the graph follows the one in FIG. 10A. For stepping frequencies up to 150 Hz, the maximum force of 100 N can still be exerted if the pressure is increased. But at higher stepping frequencies (200 Hz and higher), the maximum force is greatly reduced.

Figure 11B:
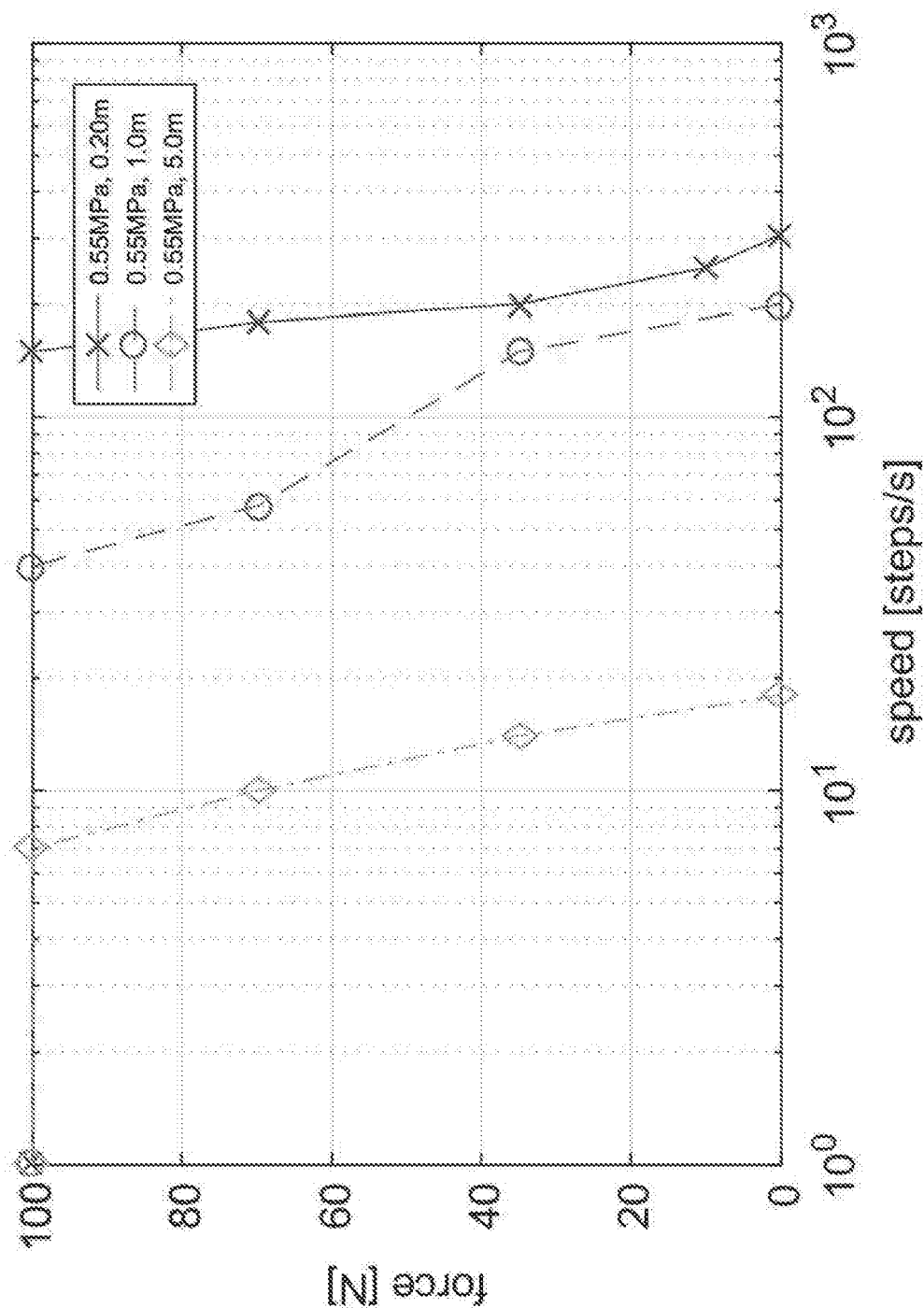
Figure 12:
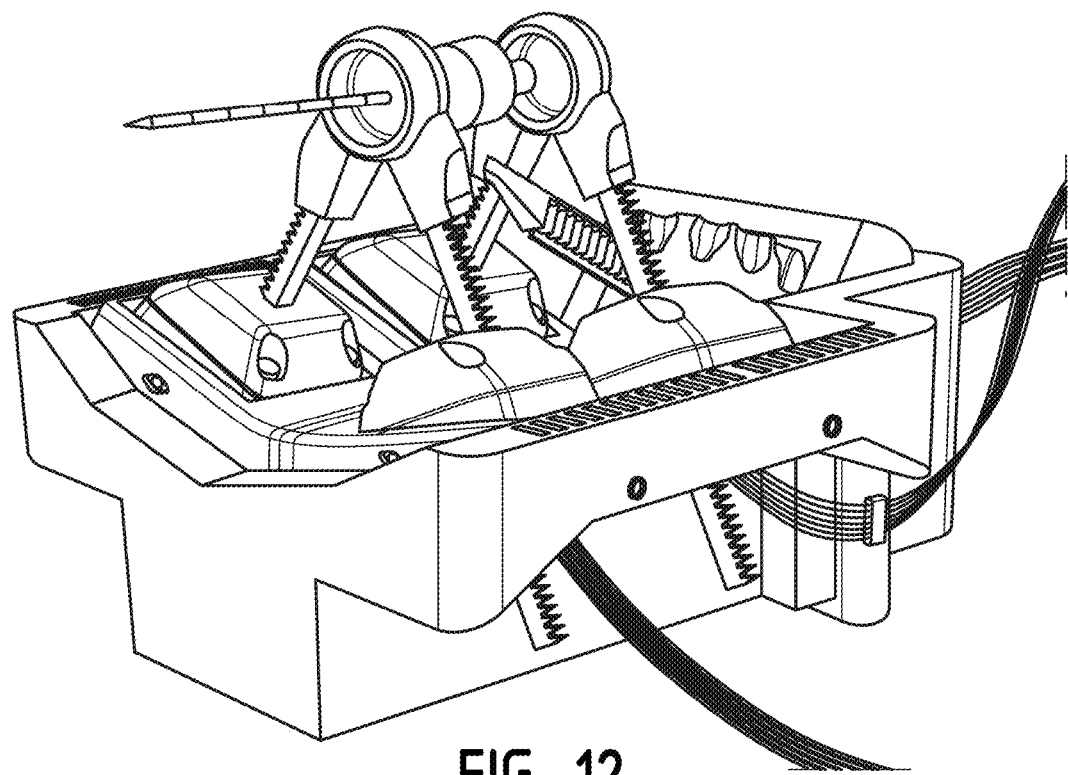

FIG. 11B shows T-49's force-speed relationship for different tube lengths (outer diameter 4 mm, inner diameter 2.5 mm), at a pressure of 0.55 MPa. As expected, using 5.0 m long tubes requires operation at much lower stepping frequency (order of 10 Hz) than when 0.20 m or 1.0 m tubes are used (order of 100 Hz).

The maximum power found for each motor is given in FIG. 26. Short tubes (0.20 m) were used. The pressure was generally set to 0.5 MPa, except for the R-44 and R-25 where the pressure was lower in order not to damage the gears. The T-63 and R-80 turned out to be the most powerful motors, both delivering around 25 W. The R-44 delivered a stable 3.7 W of power. When the frequency was increased from 75 Hz to 125 Hz, delivering 6.2 W for a short time, the gear broke down. The R-25 managed to deliver 1.1 W of power, and also broke down when the frequency was increased further.

FIG. 23 lists the developed motor's specifications alongside with state-of-the-art metal-free bidirectional pneumatic stepper motors. The T-63 motor is able to deliver 330 N of force, which is over ten times stronger than the two other linear stepper motors found in literature. The T-63 also never broke down and the teeth showed no signs of wear after extensive testing, which means that the pressure and load could be increased further and the motor has high durability.

The R-80 delivers up to 3.7 Nm, but it broke down shortly after that so the practical maximum is somewhat lower. For example, the maximum operating pressure could be limited to 0.4 MPa for this motor, resulting in an effective maximum torque of 2.5 Nm. Still, this figure is at least three times stronger than the most powerful rotational motors found in literature.

Comparing motors in terms of delivered power is not straightforward. There are no standardized testing protocols, so wattage measurements depend on the actual setup used such as tubing dimensions and valve specifications. The PneuStep delivers 3 W during normal operation, but also claimed to have delivered 37 W when pushed for power. The R-80 and T-63 both managed to deliver 25 W; especially in case of the R-80 more measurements are needed to investigate the durability of the motor at such wattages to find out the long-term maximum operating limits. On the other hand, if we are free to choose stronger non-metallic materials such as PEEK or ceramics, which PneuStep also does, then the absolute operating limits will be significantly extended and the measured 25 W of power could then be considered to be within normal operating range.

The T-63 and R-80 may be too bulky for small-size applications such as MRI-compatible robotics. Therefore, miniaturized versions of these motors have been developed as well. As the amount of work performed per step is proportional to the stroke displacement volume, downsizing one motor design results in a performance scaled down roughly proportional to its volumetric size. The T-49 has shown to be a compact and robust linear motor, delivering 100 N of force. An example application is the MRI-compatible Stormram 3 robot shown in FIG. 12 which is driven by one modified T-49 motor and four laser-cut motors. The R-44 and R-25 are also compact, but not robust yet. The gears need to be constructed from stronger materials to avoid breaking down at high loads. The main reason is that one single tooth has to bear the full load, while in the linear motors the total load is evenly distributed over four or five teeth.

Certain applications, such as MRI-compatible robots, require the valves to be placed a certain minimum distance away from the motors. In case of MRI-compatible robotics, this distance is in the order of 5 m (except when placing the valves in a shielded enclosure within the MRI room). The maximum stepping frequency of the T-49 motor over a distance of 5 m was measured to be 7 Hz when maximum force is needed. If this frequency is too low, then valves with higher airflow and/or thicker tubes are required to increase the stepping frequency to the desired level. For distances of 1 m, the maximum stepping frequency was measured to be 40 Hz, and for very short tubes the T-49 motor can be operated at up to 150 Hz while maintaining the maximum force of 100 N.

After the development of Stoianovici's PneuStep in 2007, multiple attempts have been made to develop metal-free pneumatic stepper motors that are compact, powerful and easy to manufacture, with limited success. Many of the previously developed motors are relatively weak or too bulky, due to the small bore sizes, inefficient mechanics, excessive leakage or other reasons. In contrast, the designs presented in this paper employ large bore sizes in a space-efficient housing with good transfer of forces, resulting in easily manufacturable motors with radically improved specifications.

Five stepper motors have been developed: two linear and three rotational ones, in sizes ranging from 25 mm to 80 mm. The T-63 and R-80 motors have shown to be significantly stronger than any other non-metallic pneumatic motor found in literature, and all motors are easy to manufacture by rapid prototyping. The presented design method involving box-shaped pistons that embrace a rack or gear, has shown to be the key concept that is likely to advance the field of metal-free pneumatic stepper motors towards a higher level.

To illustrate the use of rapid prototyping high-performance metal free pneumatic stepper motors, the clinical application of these type of motors in the design of an new MRI compatible robotic system for breast biopsy is presented below. In the diagnosis phase of breast cancer, targeting of small lesions with high precision is essential. This influences accurate follow-up and subsequently determines prognosis. Current techniques to diagnose breast cancer are suboptimal, and there is a need for a small, MRI-compatible robotic system able to target lesions with high precision and direct feedback of MRI. Therefore, the design and working mechanism of the new Stormram 4, an MRI-compatible needle manipulator with four degrees of freedom, will be presented to take biopsies of small lesions in the MRI scanner. Its dimensions (excluding racks and needle) are 72×51×40 mm, and the system is driven by two linear and two curved pneumatic stepper motors. The T-26 linear motor measures 26×21×16 mm, has a step size of 0.25 mm and can exert 63 N at 0.65 MPa. The workspace has a total volume of 2.2 L.

Accuracy measurements have shown that the mean positioning error is 0.7 mm, with a reproducibility of 0.1 mm. Consequently, these preliminary results show that the robot might be able to target millimeter-sized lesions for the MRI-guided breast biopsy procedure.

Breast cancer is one of the most frequently diagnosed cancer types with an estimated 1.67 million new cancer cases in 2012, and the leading cause of cancer-related death among women worldwide. In breast cancer screening, suspicious lesions need to be biopsied for pathological confirmation of the diagnosis. Some abnormalities are occult on mammography and ultrasound and can only be detected with MRI. In these cases a biopsy will be taken of the, often small, suspicious lesion under MRI-guidance. In current clinical practice, the needle must be inserted manually with the patient moved in and out of the scanner-bore multiple times for position adjustment and verification.

This phase of the biopsy procedure is time-consuming and because of deformations due to needle-tissue interactions and patient movements, the needle may need to be repositioned by using an alternate trajectory or multiple insertions leading to additional tissue damage and inaccurate placement.

Increased needle positioning accuracy and efficiency using a robotic system could improve the standard of care for women with a MRI detected lesion. If such a system is able to insert the needle inside the MRI scanner and is MRI-compatible itself, (near-)realtime imaging feedback is possible and enhances accuracy. Therefore, the aim of this project was to design and characterize an MRI-compatible robotic system for breast biopsy.

Previous studies showed the design of robotic systems in several applications inside the MRI scanner. Stoianovici et al. developed the MrBot, a six DOF robotic system for prostate biopsy and driven by pneumatic rotational stepper motors. Franco et al. developed a four DOF robot for liver biopsy, driven by pneumatic cylinders with a new time-delay control scheme. Hungr et al. developed a five DOF robotic system driven by a combination of ultrasonic motors, Bowden cables and pneumatic actuators. Bomers et al. developed a five DOF robot driven by pneumatic linear stepper motors for transrectal prostate biopsy guidance.

The authors of the current paper, Groenhuis et al., developed three robotic systems for breast biopsy. The Stormram 1 is a seven DOF needle manipulator driven by 72 mm-sized pneumatic linear stepper motors with a force of 24 N. For the Stormram 2, the motors were miniaturized to fit inside 45 mm-sized ball joints and driven by a computerized valve manifold. The Stormram 3 has five degrees of freedom, and with improved accuracy and workspace, and utilizes the T-49 stepper motor which can exert 100 Newton so that more dense tissue can be targeted.

The described robots are all parallel manipulators. While such a kinematic chain increases structural rigidity, it also limits the workspace and makes forward/inverse kinematics relatively complicated. The Stormram 3 also cannot move the needle along a straight path.

Our approach is to use a serial kinematic chain, driven by a combination of linear and novel curved pneumatic stepper motors. If rigidity can be preserved under the absence of metallic materials, a serial kinematic chain offers important advantages in terms of structural/kinematic complexity, controllability and workspace size. The robot can be made inherently MRI safe by the choice of materials and using pneumatic actuation.

The presented Stormram 4 robot is a needle manipulator with four degrees of freedom placed in a serial kinematic chain. The four joints are actuated by pneumatic stepper motors. In its home position 13, the robot (excluding needle and racks) measures 72×51×40 mm.

Figure 14:
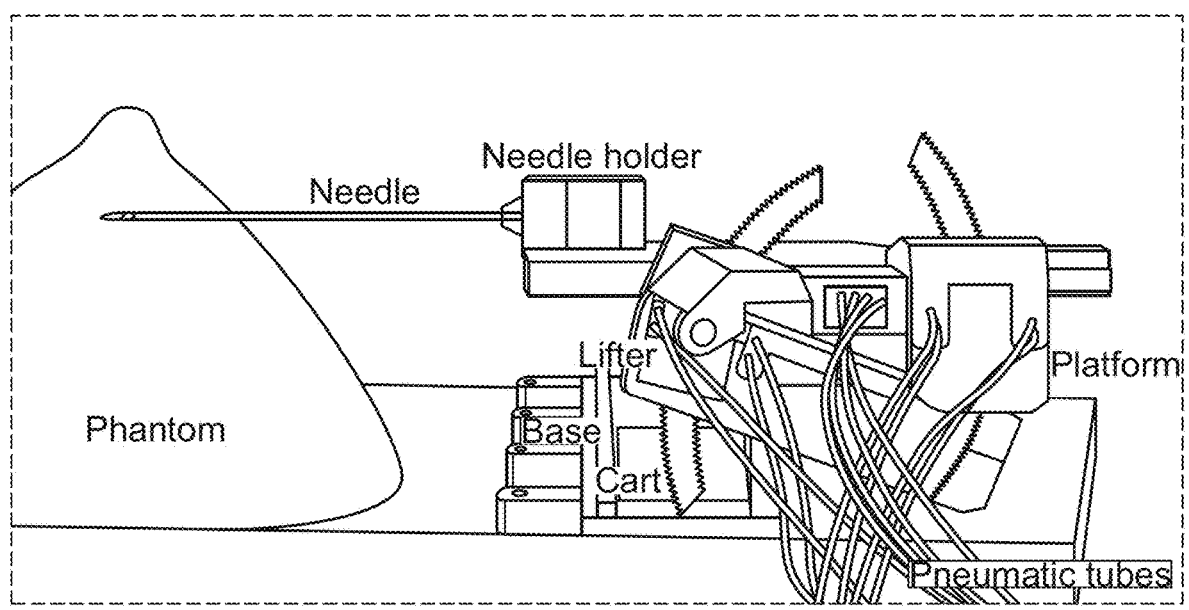

FIG. 14 shows the different part of the robot. The base is fixed and has a rack, on which the cart can slide back and forth over a distance of 160 mm. The cart itself contains a curved rack, which the lifter uses to tilt itself upwards over an angle up to 47°. Likewise, the lifter has another curved rack on which the platform can tilt to the other side over an angle up to 38 degree. Finally, the platform drives a needle holder back and forth over a distance of 80 mm, on which the needle itself is mounted to target a breast phantom. Sixteen pneumatic tubes guide air to the different chambers of the four motors. The mass of the Stormram 4 (without base) is 62 g.

Figure 15:
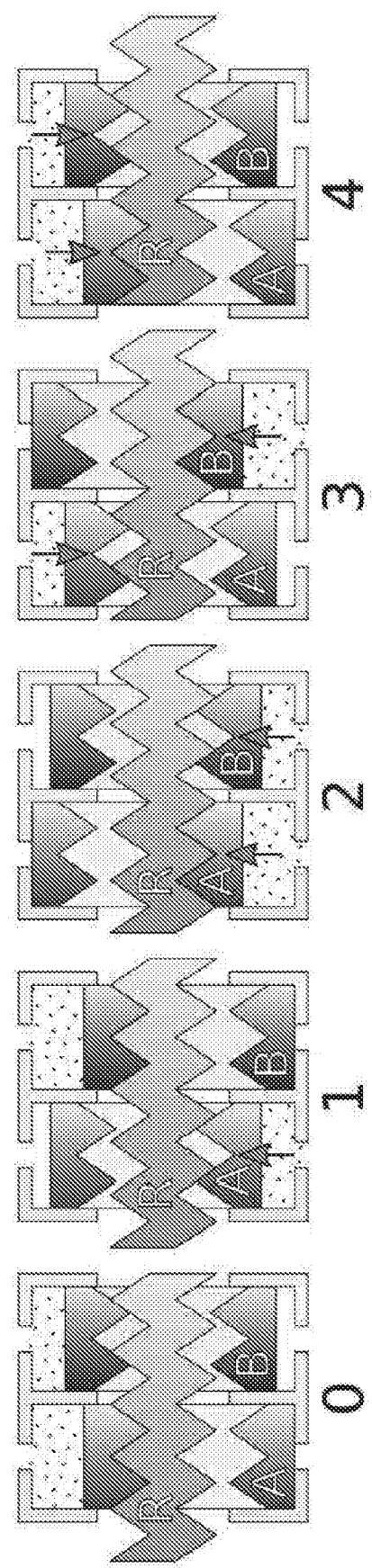

Two different stepper motors have been developed for the Stormram 4: the T-26 linear motor, and the C-30 curved motor. The general mechanism is shown in FIG. 15. It shows a rack R and two double-acting pistons A, B. Each piston consists of two piston heads, with jaws on the inside that engage on the rack by means of a wedge mechanism. By pressurizing the four chambers with appropriate waveforms, the pistons push the rack step by step in the desired direction. By design, the motor has zero backlash and nonzero hysteresis. The reason is that both pistons simultaneously push on the rack, but only one can be at its extreme position as can be seen in FIG. 15.

The T-26 linear stepper motor is a miniaturization of the T-49 motor described above. The T-26 measures 26×21×16 mm. The two cylinders inside this motor have a square cross-sectional area of 10×10 mm=100 mm². The pistons act on a straight rack with teeth pitch 1.0 mm and teeth depth 1.2 mm. The step size is 0.25 mm, which is one-quarter of the pitch. The wedge ratio is $$\frac{1.2}{0.5} = 2.4,$$

so at a pressure of 0.4 MPa the theoretical output force is $F=0.4 \cdot 10^6 \cdot 100 \cdot 10^{-6} \cdot 2.4=96$ N, or 240 N/MPa. Due to friction in the seals and other sliding parts, the measured output force will be lower. If desired, the pressure can be increased to compensate for it and generate higher forces.

Figure 16:
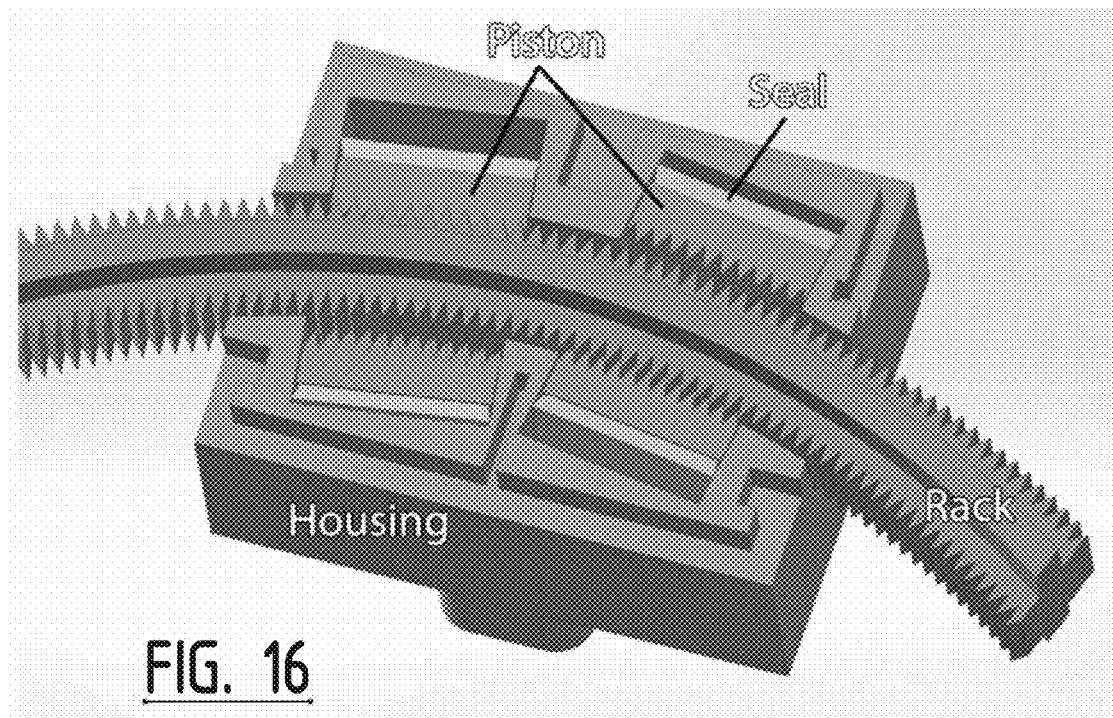

The C-30 curved stepper motor is a novel design and measures 30×23×14 mm (excluding tube sockets). A 3-D rendering of the C-30 (without top cover) is shown in FIG. 16. The C-30 also houses two cylinders with the same square cross-sectional area of 100 mm² as in the T-26 linear stepper motor. The difference is that the rack is not straight, but has a radius of curvature of 50 mm. The teeth pitch size is 1.0°, which corresponds to an effective pitch distance of 0.87 mm on a circle with radius 50 mm. The step size is 0.25°, which is one quarter of the pitch size. The teeth depth is 1.2 mm. At a pressure of 0.2 MPa, the theoretical output torque is $$M = 0.2 \cdot 10^6 \cdot 100 \cdot 10^{-6} \cdot 1.2 \cdot 10^{-3} \cdot \frac{180}{0.5\pi} = 138 \text{ Nm},$$

or 55 N at an arm length of 50 mm. Similar to the T-26 motor, the measured output force will be lower due to friction in the seals and other sliding pars, which can be compensated by increasing the pressure.

The curved stepper motor has an axis of rotation. Therefore, a physical joint driven by this actuator can be combined with a passive pin joint with small radius, placed at the axis of rotation. This is useful to significantly increase the rigidity of the joint. In the linear stepper motor this would not be an option, as its axis of rotation is located at infinity.

The parts of the Stormram 4 were printed with the Stratasys Objet Eden260 (Stratasys Ltd., Eden Prairie, MN, USA) in FullCure720 material. The seals were laser-cut from 0.5 mm thick silicone rubber. The motor housing and cover were glued together, and the sixteen polyurethane tubes were also glued into the sockets. The base was laser-cut from an 8 mm plate, engraved with grooves in which the linear rack and guide rail were glued.

Figure 17:
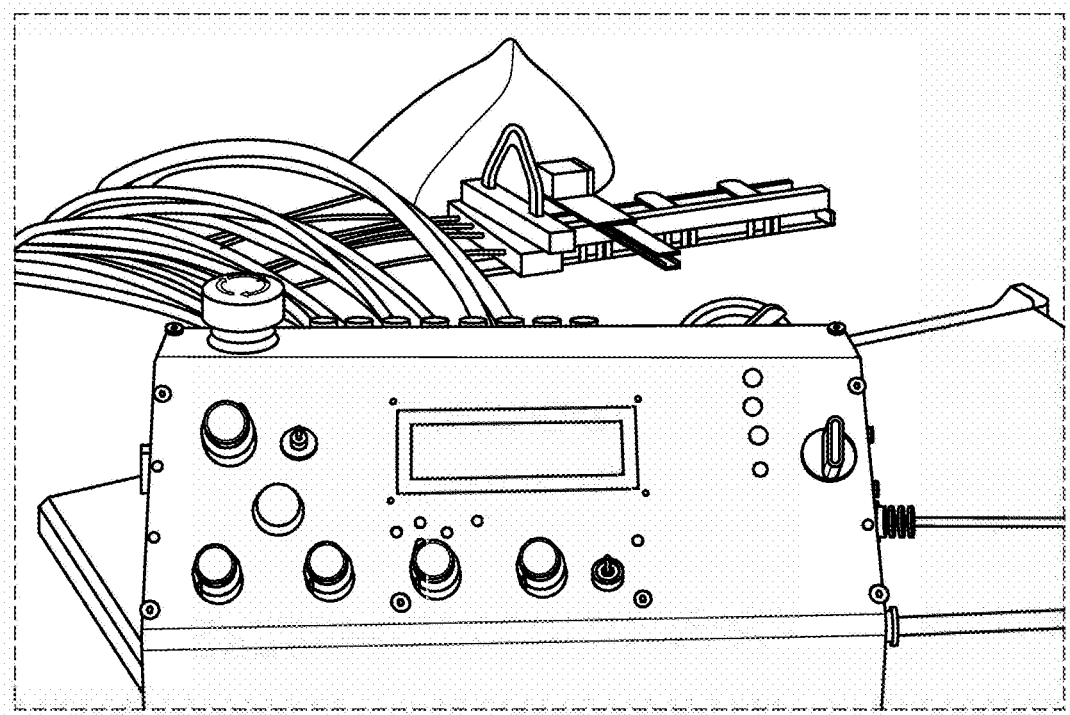

The robot is controlled by a pneumatic valve manifold, shown in FIG. 17. The valves are of type Festo MHA2-MS1H-5/2-2, and are controlled with an Arduino Mega board. Eight valves control the four actuators of the robot. One valve is connected to a pressure sensor for tube length measurements, and the remaining valves are reserved for future extensions such as a needle firing mechanism.

A user interface allows to control the robot in different ways. The stepping frequency is controlled by a turn knob. The maximum frequency is 60 Hz when 0.5 m tubes are connected. In manual control mode, the four turn knobs on the bottom row reflect the setpoints of the four joints and the robot can be directed to the right position manually. In automatic mode, the controller navigates the robot through a pre-programmed sequence of setpoints.

The display shows the joint configuration vector or the needle tip position and orientation. Pushbuttons allow to cycle through different information panels and enable various actions such as calibration or automatic mode initiation. Voltage and pressure sensors examine operational status. Upon loss of pressure or voltage, the valves are switched off and the current joint coordinates are stored in memory.

Figure 18:
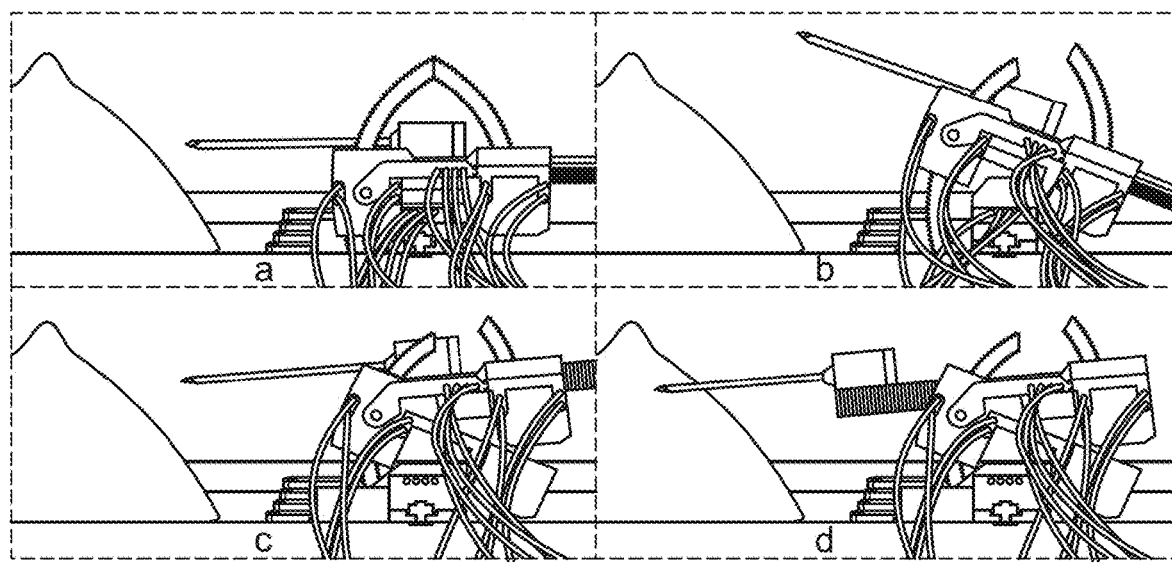

FIG. 18 shows a sequence of states during the needle alignment and insertion process. It shows the effect of actuation of three different joints, allowing to align and insert the needle in the YZ-plane towards a given location.

Figure 19:
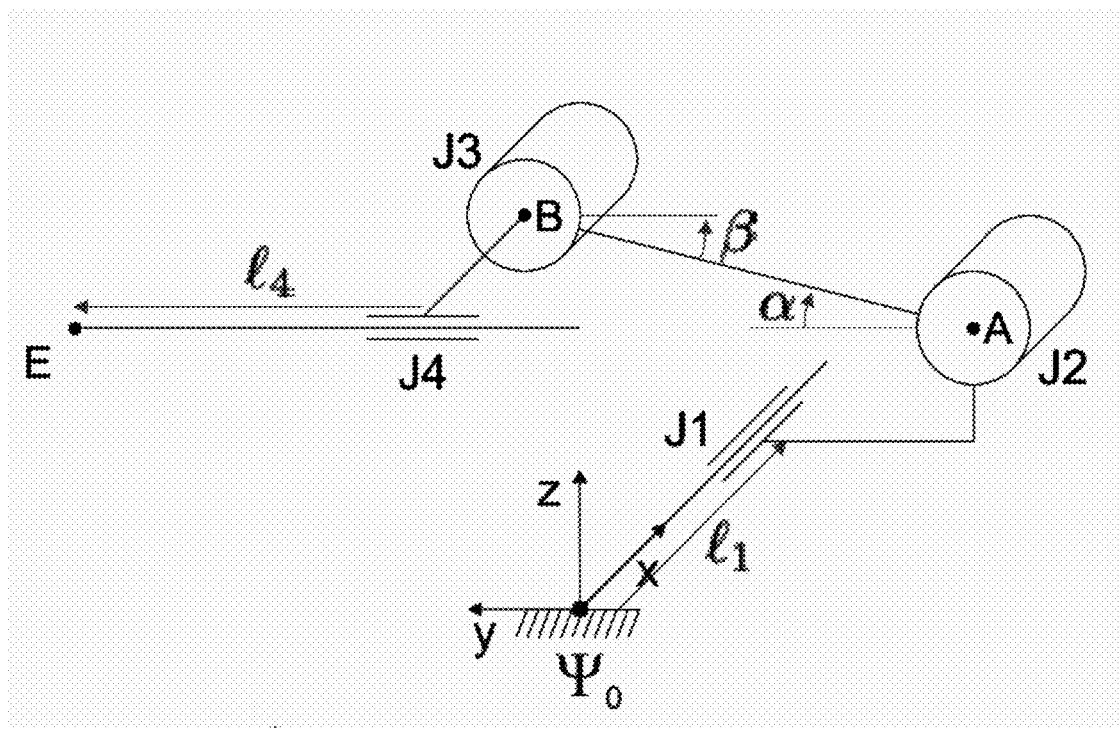

FIG. 19 shows the kinematic configuration of the Stormram 4. Kinematically, it is a serial manipulator with four actuated joints. J1 and J4 are prismatic joints, driven by linear stepper motors. Joints J2 and J3 are rotational joints, driven by curved stepper motors. Point E is the end-effector, physically the tip of the needle. Its coordinates are ($E_x$, $E_y$, $E_z$, $E_\phi$), in which $E_\phi$ is the rotation angle around the X-axis.

The joint configuration vector v=($\ell_1$, α, β, $\ell_4$) defines the pose of the full robot. The range of these variables are:

$\ell_1$:0–160 mm

α:0°–47°

β:0°–38°

$\ell_4$:65–145 mm

The step size of $\ell_1$ and $\ell_4$ is 0.25 mm, and the step size of a and is 0.25°.

In order to translate v to position and orientation of E and vice-versa, forward and inverse kinematics are derived.

The end-effector coordinates are calculated as follows:

$E_x = \ell_1$ $E_y = Y_0 + W_1 \cos\alpha - H_2 \sin(\alpha-\beta) + \ell_4 \cos(\alpha-\beta)$ $E_z = H_1 + W_1 \sin\alpha + H_2 \cos(\alpha-\beta) + \ell_4 \sin(\alpha-\beta)$ $\phi = \alpha - \beta$ The constants are:

$Y_0 = -61$ mm, $H_1 = 15$ mm, $W_1 = 50$ mm, $H_2 = 18$ mm

Given the desired end-effector location and orientation ($E_x$, $E_y$, $E_z$, $\phi$), the joint vector v=($\ell_1$, α, β, $\ell_4$) was calculated. Geometrically, this is equivalent to one particular intersection of a line with a circle in the YZ-plane. We first transformed ($E_y$, $E_z$) to ($E'_y$, $E'_z$), and then found an expression involving $\ell_4$:

$E'_y = E_y + H_2 \sin\phi - Y_0$ $E'_z = E_z - H_2 \cos\phi - H_1$ $W_1^2 = (E'_y - \ell_4 \cos\phi)^2 + (E'_z - \ell_4 \sin\phi)^2$ Solving for $\ell_4$ and taking the solution with smallest value, leads to:

$\ell_1 = E_x$ $\ell_4 = E'_y \cos\phi + E'_z \sin\phi - \sqrt{(E'_y \cos\phi + E'_z \sin\phi)^2 - E'^2_y - E'^2_z + W_1^2}$ $\alpha = \arcsin\dfrac{E'_z - \ell_4 \sin\phi}{W_1}$ $\beta = \alpha - \phi$ The solution is valid if $\ell_4$ is real, and all parameters ($\ell_1$, α, β, $\ell_4$) are within the ranges.

Due to discretization of the stepper motors, the actual value of the four parameters must be a multiple of its step size (0.25 mm or 0.25 degree). The general approach is to round each parameter to its nearest reachable value, leading to end-effector positioning errors of the same order as the step size. This error could be reduced if the angle φ can be chosen: the optimal angle φ is the one (within its allowed range) which minimizes the end-effector positioning error.

Figure 20:
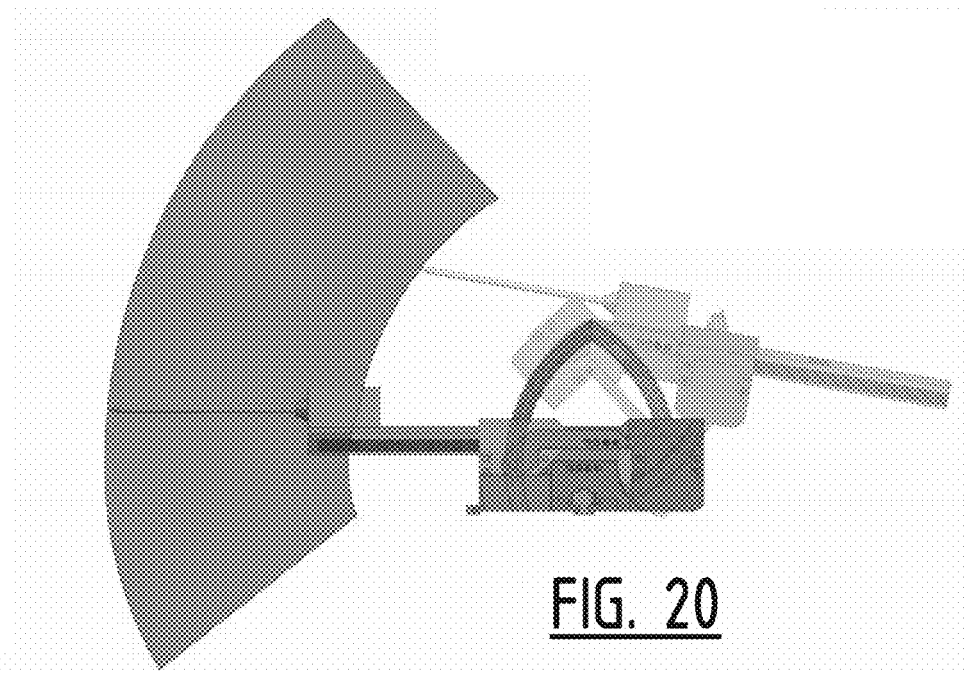

FIG. 20 shows the projection of the robot on the YZ plane in two different poses. One pose has configuration vector v=(0 mm, 47°, 38°, 65 mm). The red area is the projected reachable space of the end-effector E, and its area is calculated to be 140 cm². The robot can move in the X-direction over a distance of 160 mm orthogonal to the YZ plane, resulting in a total workspace volume of 2.2 L.

Performance measurements of the stepper motors and measurements on Stormram 4's positional accuracy have been performed to characterize the Stormram 4.

Figure 21:
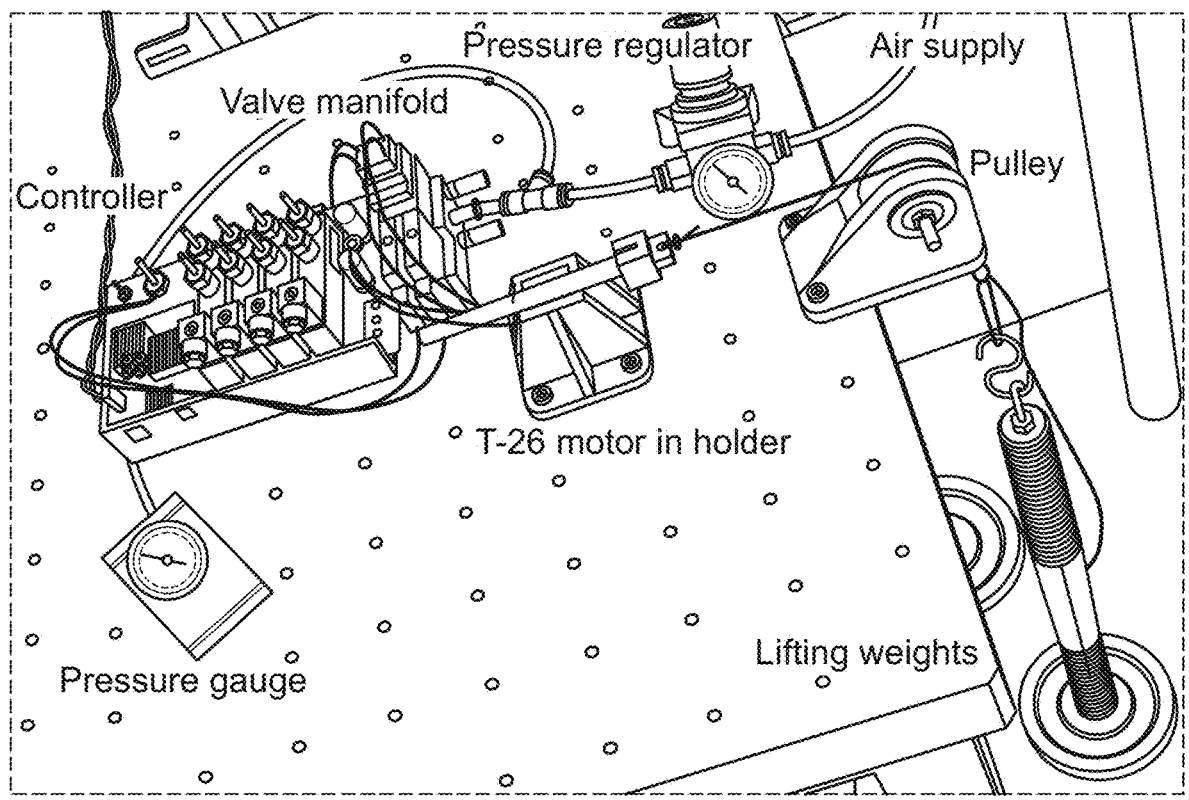
Figure 22:
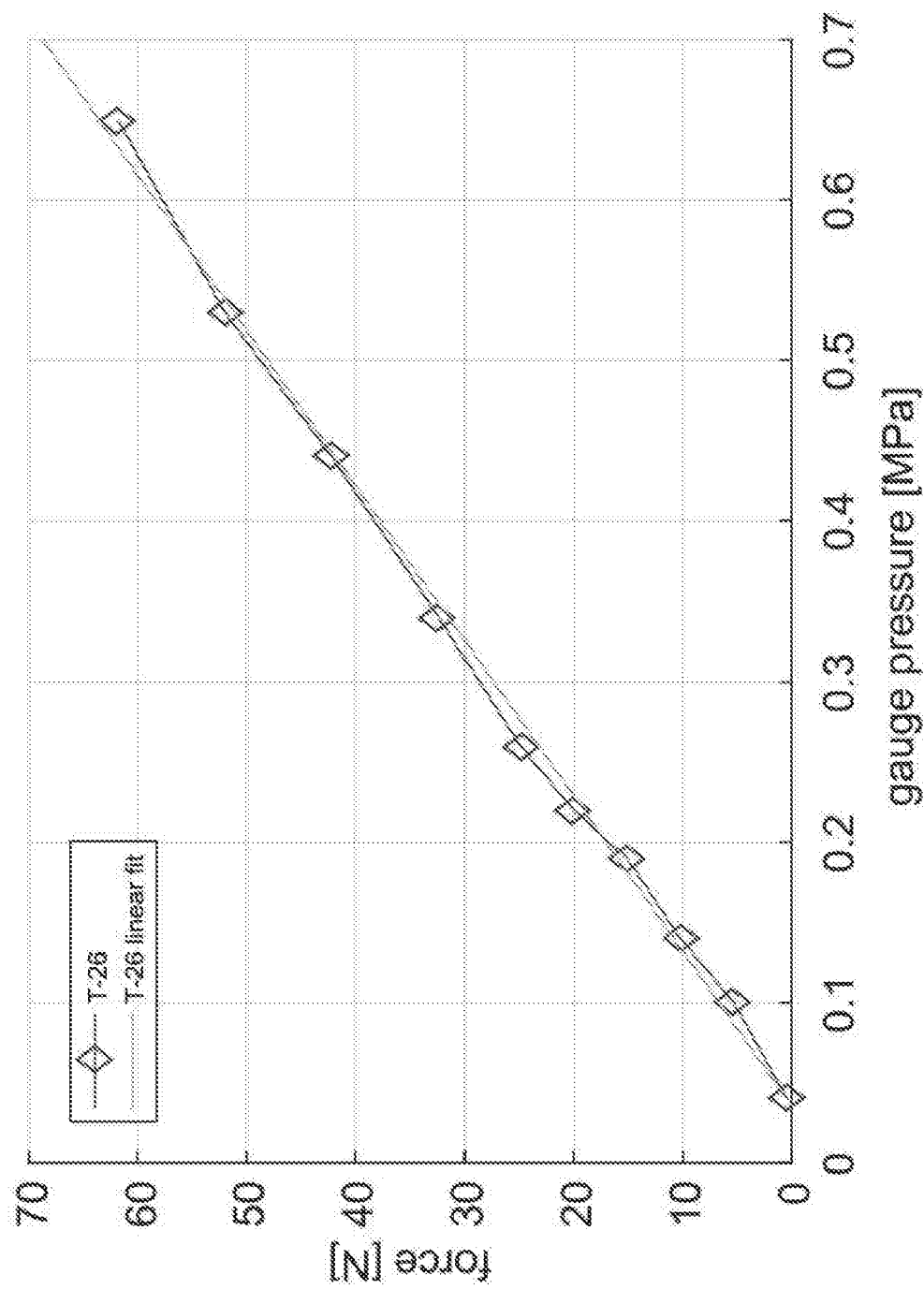

The T-26 linear stepper motor has been evaluated using a test bench shown in FIG. 21. For a range of known masses, the minimum pressure on which the motor could lift the weight was recorded. The results are shown in FIG. 22. The highest measured force was 63 N, at a pressure of 0.65 MPa.

It can be observed that the graph is approximately linear. Its slope is 103 N/MPa. This results in a mechanical efficiency of 43%, when compared with the theoretical force slope of 240 N/MPa.

Figure 13:
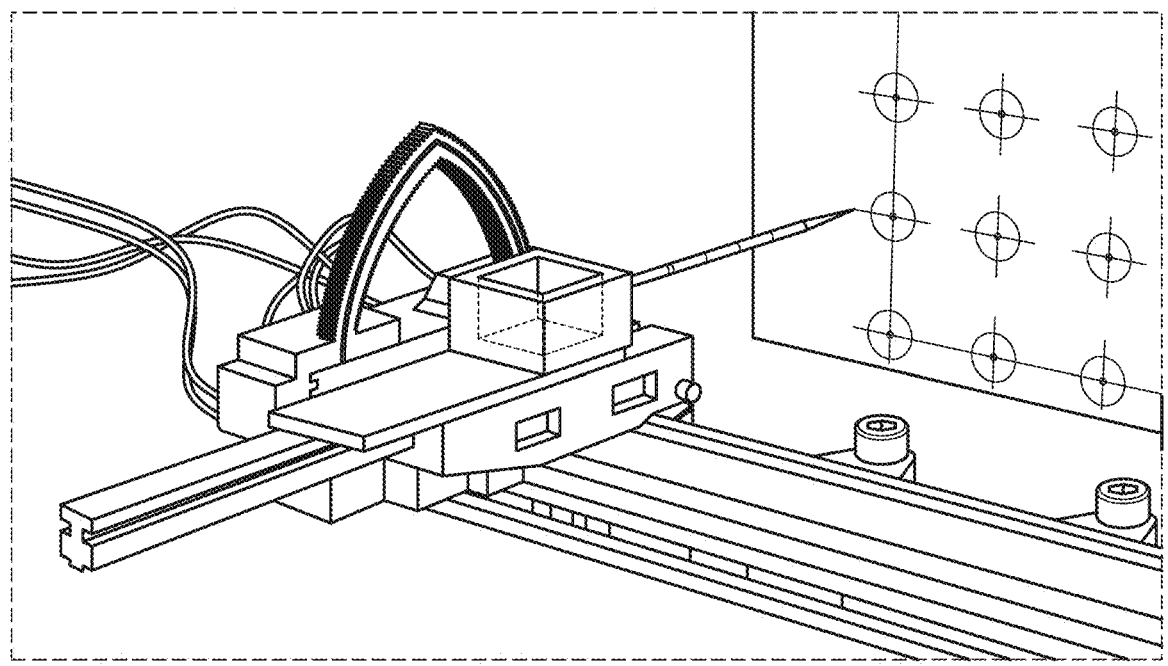

The positional accuracy was evaluated using a sheet of paper positioned in the Y=80 mm plane, as shown in FIG. 13. On this sheet, a 7×5 grid of targets with 25 mm spacing was drawn. The robot was programmed to move to these targets in succession, resulting in a series of punctures in the sheet. Afterwards, the X and Z offsets of each puncture (relative to its target) were measured.

The mean target-puncture offsets and the standard deviations were calculated for all 35 data points, and are listed in FIG. 27. It was observed that the offsets show a strong correlation with the Z coordinate, which implies that the axes of the J2 and/or J3 joints are not exactly parallel to the X-axis, causing small systematic offsets. When this is taken into account, the average standard deviation for each value of Z was calculated to be 0.17 mm.

A repeatability experiment was performed by executing the same travel path again. For all 35 targets, the needle reached the same spot as in the first run, so no new punctures were created. Considering the size of the puncture (diameter 0.20 mm), the repeatability is therefore lower than 0.10 mm.

For comparison with the previous version, the properties of the current Stormram 4's T-26 and the T-49 stepper motor of the Stormram 3 are listed in FIG. 28. The T-26 has less than half the strength of the T-49, but the dimension has been reduced approximately a factor two in all directions and the step size was reduced by a factor four.

The positional accuracy of the Stormram 4 is 0.71 mm in X direction, and 0.21 mm in Y direction. This shows that sub-millimeter precision is achieved, which is a significant improvement over the Stormram 3. An important reason is the simplicity of the kinematic design: there are only four joints, and as all of these are directly actuated, the kinematic chain is fully free of backlash. There is a small systematic error with a maximum of 1.0 mm, apparently caused by slight misalignment of axes in the Stormram 4 resulting from the 3-D printing manufacturing process. If the systematic errors are compensated for, by e.g. precise calibration of the physical geometries, the accuracy can be further improved to 0.17 mm in both X and Y directions. In future iterations of the robot, the structural rigidity could be improved by e.g. duplicating the J2 and J3 joints to the other side of the robot.

The step size is 0.25 mm (for the linear motors). When short tubes of 0.5 m are used, the motors can run at speeds as high as 60 Hz, resulting in a movement speed of 15 mm/s. However, in a MRI setting the maximum stepping frequency is in the order of 10 Hz, and results in a lower movement speed of approximately 2.5 mm/s. This might be too slow for the breast biopsy procedure. A solution would be to use a larger step size of 0.5 mm, which doubles the travel speed at the cost of reduced accuracy. A different solution would be to drive a single joint with two motors, to achieve both high speed and high precision.

The next step to evaluate the performance of the Stormram 4 in a more realistic clinical setting is to perform MRI tests on breast phantoms. The effect of the increased tube length (due to separation of MRI-compatible robot and MRI unsafe controller) on the Stormram 4 performance should also be taken into account. Other aspects include the implementation of a needle firing mechanism, which enables sampling of tissue from a suspicious lesion. In addition, a more robust design could be made by duplicating certain joints, especially J2 and J3. This would increase overall stiffness and therefore reduce the systematic error.

The Stormram 4 has demonstrated that it is able to manipulate a needle towards targets with sub-millimeter precision and an insertion force of approximately 40 N. The actuators are free of backlash, and on short distances the maximum speed is 15 mm/s.

The linear and curved motors are significantly smaller with a size of 26 and 30 mm, than the state-of-art motors, and these are efficiently integrated in the different parts of the robot. The novel curved motor has shown that it can actuate a revolute joint with high precision. Due to the serial kinematic chain the number of moving parts are reduced to an absolute minimum, resulting in a design that is compacter than state-of-art robots.

Further tests on breast phantoms in a MRI scanner will be performed to simulate targeting lesions and also take tissue deformations into account. A breast fixation system and a biopsy firing mechanism are improvements to implement the full MRI-guided biopsy procedure in the design. As a proof-of-concept, the Stormram 4 has shown that it is a suitable system to implement in clinical breast biopsy procedures.

V. Groenhuis and S. Stramigioli, "Laser-Cutting Pneumatics," in IEEE/ASME Transactions on Mechatronics, vol. 21, no. 3, pp. 1604-1611. June 2016. doi: 10.1109/TMECH.2015.2508100

V. Groenhuis, J. Veltman and S. Stramigioli, "Stormram 2: A MRI-compatible pneumatic robotic system for breast biopsy," Proceedings of The Hamlyn Symposium on Medical Robotics, June 2016, Imperial College and the Royal Geographical Society, London, UK, pp. 52-53.

Whitney, J. P., Glisson, M. F., Brockmeyer, E. L., and Hodgins, J. K., "A low-friction passive fluid transmission and fluid-tendon soft actuator." In 2014 IEEE/RSJ International Conference on Intelligent. Robots and Systems (pp. 2801-2808).

R. Gassert, R. Moser, E. Burdet, and H. Bleuler, "MRI/fMRI-compatible robotic system with force feedback for interaction with human motion," IEEE/ASME Trans. Mechatronics, vol. 11, no. 2, pp. 216-224, 2006.

Su, H., Zervas, M., Cole, G. A., Furlong, C., and Fischer, G. S, "Real-time MRI-guided needle placement robot with integrated fiber optic force sensing." In Robotics and Automation (ICRA), 2011 IEEE International Conference on (pp. 1583-1588). IEEE.

P. Moreira, S. Misra, "MR-Compatible Robot for Needle-Based Prostate Interventions." Proceedings of The Hamlyn Symposium on Medical Robotics 25-28 Jun. 2016, Imperial College London and the Royal Geographical Society, London, UK Chapuis, D., Gassert, R., Ganesh, G., Burdet, E. A. B. E., and Bleuler, H. A. B. H, "Investigation of a cable transmission for the actuation of MR compatible haptic interfaces." The First IEEE/RAS-EMBS International Conference on Biomedical Robotics and Biomechatronics, 2006. BioRob 2006. (pp. 426-431).

Chapuis, D., Gassert, R., Ganesh, G., Burdet, E. A. B. E., and Bleuler, H. A. B. H., "Investigation of a cable transmission for the actuation of MR compatible haptic interfaces." In The First IEEE/RAS-EMBS International Conference on Biomedical Robotics and Biomechatronics, 2006. BioRob 2006. (pp. 426-431).

Felfoul, O., Becker, A., Bergeles, C., and Dupont, P. E, "Achieving commutation control of an MRI-powered robot actuator." IEEE Transactions on Robotics, 31(2), 387-399 (2015).

Elhawary, H., Zivanovic, A., Tse, Z. T. H., Rea, M., Davies, B. L., Young, I, Bydder, G., Payley, M. and Lamperth, M. U., "A magnetic-resonance-compatible limb-positioning device to facilitate magic angle experiments in vivo." Proceedings of the Institution of Mechanical Engineers, Part H: Journal of Engineering in Medicine, 222(5), 751-760.

Comber, D. B., Slightam, J. E., Barth, E. J., Gervasi, V. R., and Webster, R. J., "Design and precision control of an MR-compatible flexible fluidic actuator." In ASME/BATH 2013 Symposium on Fluid Power and Motion Control. American Society of Mechanical Engineers, 2013

B. Yang, U. X. Tan, A. B. McMillan, R. Gullapalli, and J. P. Desai, "Design and control of a 1-DOF MRI-compatible pneumatically actuated robot with long transmission lines," IEEE/ASME Trans. Mechatronics, vol. 16, no. 6, pp. 1040-1048, 2011.

Y. Chen, C. D. Mershon, Z. Tsz, and H. Tse, "A 10-mm MR-Conditional Unidirectional Pneumatic Stepper Motor," IEEE/ASME Transactions on Mechatronics, Vol. 20, no. 2, April 2015, pp. 782-788.

Stoianovici, D., Patriciu, A., Petrisor, D., Mazilu, D., and Kavoussi, L., "A new type of motor: pneumatic step motor." IEEE/ASME Transactions On Mechatronics, 12(1), 98-106, 2007.

H. Sajima, I. Sato, H. Yamashita, T. Dohi, and K. Masamune, "Two-DOF non-metal anipulator with pneumatic stepping actuators for needle puncturing inside open-type MRI," World Autom. Congr. (WAC), 2010, no. 1, pp. 3-8, 2010.

Sajima, H., Kamiuchi, H., Kuwana, K., Dohi, T., and Masamune, K., "MR-safe pneumatic rotation stepping actuator." Journal of Robotics and Mechatronics, Vol. 24, No. 5, 2012, pp. 820-827, 2012.

Y. Chen, K. W. Kwok, and Z. T. H. Tse, "An MR-Conditional High-Torque Pneumatic Stepper Motor for MRI- Guided and Robot-Assisted Intervention," Ann. Biomed. Eng., vol. 42, no. 9, pp. 1823-1833, 2014.

Secoli, R., Robinson, M., Brugnoli, M., and y Baena, F. R., "A low-cost, high-field-strength magnetic resonance imaging-compatible actuator." Proceedings of the Institution of Mechanical Engineers, Part H: Journal of Engineering in Medicine, 229(3), pp. 215-224, 2015.

Z. Guo, T. T. L. Lun, Y. Chen, H. Su, D. T. M. Chan, K. W. Kwok, "Novel Design of an MR-safe Pneumatic Stepper Motor for MRI-guided Robotic Interventions," Proceedings of The Hamlyn Symposium on Medical Robotics 25-28 Jun. 2016, Imperial College London and the Royal Geographical Society, London, UK, pp. 50-51.

J. Ferlay, I. Soerjomataram, M. Ervik, K. Dikshit, S. Eser, C. Mathers, M. Rebelo, D. Parkin, D. Forman, F. Bray. GLOBOCAN 2012 v1.0, Cancer Incidence and Mortality Worldwide: International Agency for Research on Cancer CancerBase; 2012 [Available from: http://globocan.iarc.fr/Pages/fact_sheets_cancer.aspx].

E. R. Price, "Magnetic resonance imaging-guided biopsy of the breast: fundamentals and finer points". Magn Reson Imaging Clin N Am, vol. 21, issue 3, pp. 571-581, 2013.

M. C. Chevrier, J. David, M. E. Khoury, L. Lalonde, M. Labelle, I. Trop, "Breast Biopsies Under Magnetic Resonance Imaging Guidance: Challenges of an Essential but Imperfect Technique". Curr Probl Diagn Radiol; vol. 45, issue 3, pp. 193-204, 2016.

J. Veltman, C. Boetes, T. Wobbes, J. G. Blickman, J. O. Barentsz, "Magnetic Resonance-Guided Biopsies and Localizations of the Breast: Initial Experiences Using an Open Breast Coil and Compatible Intervention Device". Investigative Radiology, vol. 40, issue 6, pp. 379-384, June 2005.

D. Stoianovici, A. Patriciu, D. Petrisor, D. Mazilu, and L. Kavoussi, "A new type of motor: pneumatic step motor." IEEE/ASME Transactions On Mechatronics, 12(1), 98-106, 2007.

E. Franco, D. Brujic, M. Rea, W. M. Gedroyc and M. Ristic, "Needle-Guiding Robot for Laser Ablation of Liver Tumors Under MRI Guidance," in IEEE/ASME Transactions on Mechatronics, vol. 21, no. 2, pp. 931-944, April 2016.

N. Hungr, I. Bricault, P. Cinquin and C. Fouard, "Design and Validation of a CT- and MRI-Guided Robot for Percutaneous Needle Procedures," in IEEE Transactions on Robotics, vol. 32, no. 4, pp. 973-987, August 2016.

J. G. R. Bomers, D. G. H. Bosboom, G. H. Tigelaar, J. Sabisch, J. J. Fütterer, D. Yakar, "Feasibility of a 2nd generation MR-compatible manipulator for transrectal prostate biopsy guidance", European Radiology, pp. 1-7, July 2016, doi:10.1007/s00330-016-4504-2

V. Groenhuis and S. Stramigioli, "Laser-Cutting Pneumatics," in IEEE/ASME Transactions on Mechatronics, vol. 21, no. 3, pp. 1604-1611, June 2016.

V. Groenhuis, J. Veltman and S. Stramigioli, "Stormram 2: A MRI-compatible pneumatic robotic system for breast biopsy," Proceedings of The Hamlyn Symposium on Medical Robotics, June 2016, Imperial College and the Royal Geographical Society, London, UK, pp. 52-53.

M. E. M. K. Abdelaziz, V. Groenhuis, J. Veltman, F. Siepel and S. Stramigioli, "Controlling the Stormram 2: An MRI-compatible Robotic System for Breast Biopsy". 2017 IEEE International Conference on Robotics and Automation (ICRA), Singapore, 2017, pp. In press.

V. Groenhuis, J. Veltman, F. J. Siepel, S. Stramigioli, "Stormram 3: An MRI-compatible robotic system for breast biopsy" in IEEE Robotics & Automation Magazine, Special Issue on Surgical Robot Challenge, pp. In press.

The invention claimed is:

1. A pneumatic stepper motor, comprising:
a housing, said housing accommodating at least part of:
a rack comprising a plurality of gear elements, said rack having a longitudinal direction; and
two pistons arranged next to each other in the longitudinal direction of the rack, each of said two pistons comprising at least two teeth, the at least two teeth of each of said two pistons being arranged to cooperate with said rack;
wherein said rack comprises said gear elements at least two longitudinal sides thereof; and
wherein at least one of said housing, said rack, and said two pistons are manufactured from a plastic material by 3D printing.

2. The pneumatic stepper motor according to claim 1, further comprising at least one pneumatic tube connected to said housing and arranged to supply air to the housing to drive said two pistons in a reciprocating movement.

3. The pneumatic stepper motor according to claim 1, wherein said rack is a substantially straight elongated rack, thereby forming a linear pneumatic stepper motor.

4. The pneumatic stepper motor according to claim 1, wherein said at least two teeth comprise first teeth, and wherein said gear elements comprise second teeth, said second teeth extending substantially orthogonal to the longitudinal direction of the rack.

5. The pneumatic stepper motor according to claim 1, wherein each of said two pistons comprises two engagement surfaces for engagement with the rack, said two engagement surfaces being substantially opposite to each other, wherein each engagement surface comprises said at least two teeth.

6. The pneumatic stepper motor according to claim 1, wherein each of said two pistons is provided with at least one seal, said seal being arranged on a side of the piston that is opposite to a side from which the teeth extend.

7. The pneumatic stepper motor according to claim 6, wherein said seal is manufactured from a silicone rubber starting material.

8. The pneumatic stepper motor according to claim 1, wherein said housing comprises a first part and a second part, the first and second part connected to each other by at least one connector; and
wherein the first and second part are sealed to each other by a sealant.

9. The pneumatic stepper motor according to claim 8, wherein the connector is selected from the list consisting of screws and glue.

10. A device, comprising at least two pneumatic stepper motors according to claim 1, the at least two pneumatic stepper motors comprising at least one linear pneumatic stepper motor in order to be able to move a predetermined part of said device in at least one linear direction along said rack of said linear pneumatic stepper motor, and at least one curved pneumatic stepper motor in order to be able to move at least part of said predetermined part in at least one curved direction along said rack of said curved pneumatic stepper motor.

11. The device according to claim 10, wherein said device is an MRI-compatible robotic system.

12. The device according to claim 11, wherein said device is an MRI-guided breast biopsy device, and wherein said at least part of the predetermined part is a needle holder that is arranged to hold a needle.

13. A pneumatic stepper motor, comprising:
a housing, said housing accommodating at least part of:
- a rack comprising a plurality of gear elements; and
- two pistons, each of said two pistons comprising at least two teeth, the at least two teeth of each of said two pistons being arranged to cooperate with said rack, wherein said rack comprises said gear elements at at least two longitudinal sides thereof, and wherein said two pistons each comprise a cavity, wherein the teeth extend in the cavity, and wherein the rack is arranged in the cavity such that the teeth face the gear elements of said rack.

* * * * *

UNITED STATES PATENT AND TRADEMARK OFFICE
CERTIFICATE OF CORRECTION

PATENT NO. : 11,898,581 B2
APPLICATION NO. : 16/326442
DATED : February 13, 2024
INVENTOR(S) : Vincent Groenhuis, Francoise Jeanette Siepel and Stefano Stramigioli It is certified that error appears in the above-identified patent and that said Letters Patent is hereby corrected as shown below:

On the Title Page

Item (73) Assignee: please correct to read --Machnet SG PTE. LTD.--

Signed and Sealed this
Thirteenth Day of August, 2024

Katherine Kelly Vidal
*Director of the United States Patent and Trademark Office*